(12) United States Patent
Haley et al.

(10) Patent No.: US 9,099,660 B2
(45) Date of Patent: Aug. 4, 2015

(54) ALKYNYL-SUBSTITUTED INDENOFLUORENES USEFUL IN ELECTRONIC AND ELECTRO-OPTICAL DEVICES

(75) Inventors: Michael M. Haley, Eugene, OR (US); Daniel T. Chase, Eugene, OR (US); Brad Rose, Eugene, OR (US); Aaron G. Fix, Eugene, OR (US)

(73) Assignee: University of Oregon, Eugene, OR (US)

( * ) Notice: Subject to any disclaimer, the term of this patent is extended or adjusted under 35 U.S.C. 154(b) by 198 days.

(21) Appl. No.: 13/704,571

(22) PCT Filed: Jun. 15, 2011

(86) PCT No.: PCT/US2011/040451
§ 371 (c)(1),
(2), (4) Date: Dec. 14, 2012

(87) PCT Pub. No.: WO2011/159763
PCT Pub. Date: Dec. 22, 2011

(65) Prior Publication Data
US 2013/0096336 A1    Apr. 18, 2013

Related U.S. Application Data

(60) Provisional application No. 61/355,107, filed on Jun. 15, 2010, provisional application No. 61/469,670, filed on Mar. 30, 2011.

(51) Int. Cl.
| | |
|---|---|
| *C07F 7/08* | (2006.01) |
| *H01L 51/00* | (2006.01) |
| *C07C 13/62* | (2006.01) |
| *C07C 22/08* | (2006.01) |
| *C07C 25/24* | (2006.01) |
| *C07C 255/52* | (2006.01) |
| *C09K 11/06* | (2006.01) |
| *H05B 33/10* | (2006.01) |
| *H01L 51/50* | (2006.01) |

(52) U.S. Cl.
CPC ............ *H01L 51/0094* (2013.01); *C07C 13/62* (2013.01); *C07C 22/08* (2013.01); *C07C 25/24* (2013.01); *C07C 255/52* (2013.01); *C07F 7/0809* (2013.01); *C07F 7/0818* (2013.01); *C09K 11/06* (2013.01); *H01L 51/0055* (2013.01); *H05B 33/10* (2013.01); *C07C 2103/52* (2013.01); *C09K 2211/1011* (2013.01); *H01L 51/5012* (2013.01); *Y02E 10/549* (2013.01)

(58) Field of Classification Search
CPC .............................. C07F 7/182; C07F 7/1892
USPC ........................................................ 556/429
See application file for complete search history.

(56) References Cited

U.S. PATENT DOCUMENTS

| | | |
|---|---|---|
| 6,690,029 B1 | 2/2004 | Anthony et al. |
| 7,385,221 B1 | 6/2008 | Anthony et al. |
| 2008/0220285 A1 | 9/2008 | Vestweber et al. |
| 2009/0149627 A1 | 6/2009 | Pan et al. |

OTHER PUBLICATIONS

Padwa et al., J. Org. Chem. (1993) 58:6429-6437.*
Chase et al., "Indeno[1,2-b]fluorenes: Fully Conjugated Antiaromatic Analogues of Acenes," *Angew. Chem. Int. Ed.* 50:1127-1130, 2011.
Miyawaki et al., "Multiple Cycloaromatization of Novel Aromatic Enediynes Bearing a Triggering Device on the Terminal Acetylene Carbon," *Tet. Lett.* 39:6923-6926, 1998.
Padwa et al., "A Comparative Study of the Decomposition of o-Alkylynyl-Substituted Aryl Diazo Ketones. Synthesis of Polysubstituted β-Naphthols via Arylketene Intermediates," *J. Org. Chem.* 58:6429-6437, 1993.
Rose et al., "Synthesis, Crystal Structures and Photophysical Properties of Electron-Accepting Diethynylindenofluorenediones," *Org. Lett.* 13:2106-2109, 2011.
International Search Report and the Written Opinion of the International Searching Authority from International Application No. PCT/US2011/040451 dated Oct. 14, 2011.

* cited by examiner

*Primary Examiner* — Porfirio Nazario Gonzalez
*Assistant Examiner* — Kofi Adzamli
(74) *Attorney, Agent, or Firm* — Klarquist Sparkman, LLP

(57) ABSTRACT

Indenofluorenes that include at least two alkynyl-containing substituents.

34 Claims, 11 Drawing Sheets

Figure 1. Molecular structure of indenofluorene 8b; ellipsoids drawn at 30% probability.

Figure 2. Crystal packing of 8b.

FIG. 4

| compd | computational[a] | | | electrochemical[b] | | | | | optical | |
|---|---|---|---|---|---|---|---|---|---|---|
| | $E_{HOMO}$ | $E_{LUMO}$ | $E_{Gap}$ | $E(A^+/A)$ | $E(A/A^-, A^-/A^{2-})$ | $E_{HOMO}$ | $E_{LUMO}$ | $E_{Gap}$ | $\lambda_{max}$[c] | $E_{Gap}$[d] |
| 3 | −5.53 | −3.03 | 2.50 | — | — | — | — | — | — | — |
| 8b/12 | −5.53 | −3.36 | 1.97 | 1.23 | −0.62, −1.16 | −5.92 | −4.07 | 1.85 | 594 | 1.98 |
| 13 | −5.62 | −3.24 | 2.38 | — | — | — | — | — | — | — |
| 14 | −5.51 | −3.46 | 2.05 | — | — | — | — | — | — | — |
| 15 | −6.00 | −4.07 | 1.93 | — | — | — | — | — | — | — |
| 16 | −6.19 | −4.14 | 2.05 | — | — | — | — | — | — | — |
| 17a | −5.51 | −3.46 | 2.05 | 1.20 | −0.69, −1.20 | −5.88 | −4.00 | 1.88 | 568 | 2.12 |
| 17b | −5.79 | −3.70 | 2.09 | 1.33 | −0.60, −1.07 | −6.01 | −4.08 | 1.93 | 561 | 2.15 |
| 17c | −5.82 | −3.74 | 2.08 | 1.35 | −0.59, −1.07 | −6.03 | −4.09 | 1.94 | 567 | 2.13 |
| 17d | −5.83 | −3.75 | 2.08 | 1.32 | −0.60, −1.10 | −6.01 | −4.09 | 1.92 | 567 | 2.13 |
| 17e | −5.43 | −3.36 | 2.07 | 1.16 | −0.69, −1.27[f] | −5.84 | −3.99 | 1.85 | 569 | 2.11 |
| 17f | −5.53 | −3.47 | 2.06 | 1.21 | −0.66, −1.20[f] | −5.90 | −4.03 | 1.87 | 570 | 2.10 |
| 17g | −5.81 | −3.75 | 2.06 | 1.25 | −0.62, −1.11 | −5.93 | −4.06 | 1.87 | 572 | 2.11 |
| 17h | −5.97 | −3.91 | 2.06 | 1.35 | −0.52, −1.00 | −6.03 | −4.16 | 1.87 | 570 | 2.11 |
| 17i | −5.89[g] | −3.83[g] | 2.06[g] | —[h] | —[h] | —[h] | —[h] | —[h] | 577 | 2.08 |
| PCBM[i] | — | — | — | 1.54 | −0.71, −1.12 | −6.2 | −3.95 | 2.35 | — | — |

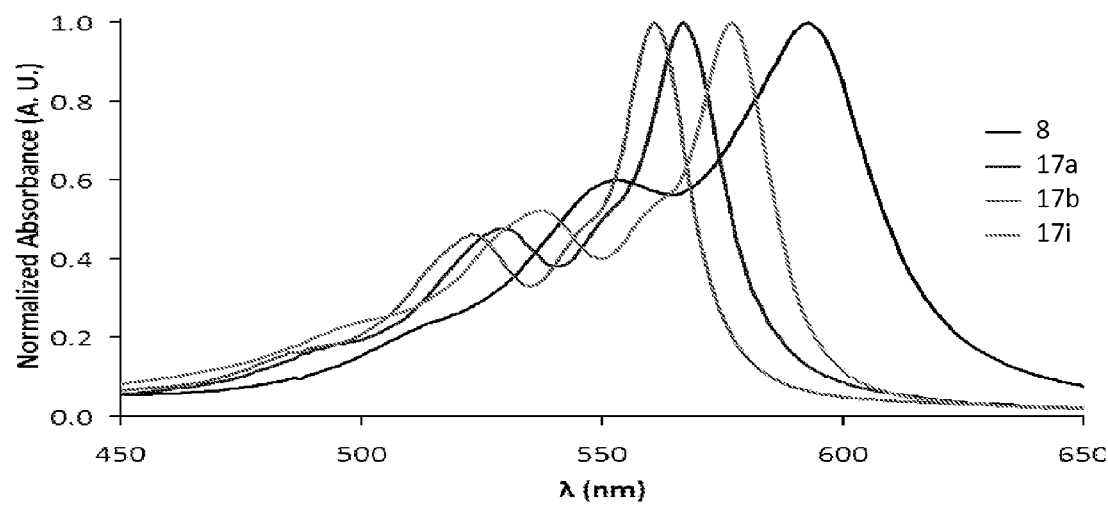
Figure 5. Electronic absorption spectra for IFs 8b and 17a,b,i.
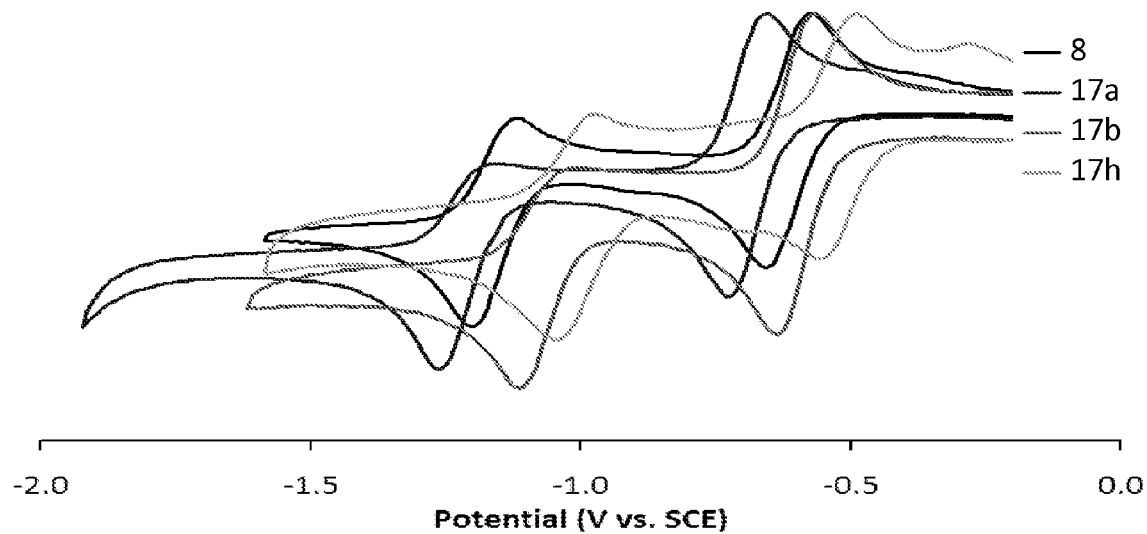
Figure 6. Cyclic voltammetry of IFs 8b and 17a,b,h; voltammogram currents are normalized to the Epa (A/A−) peak.

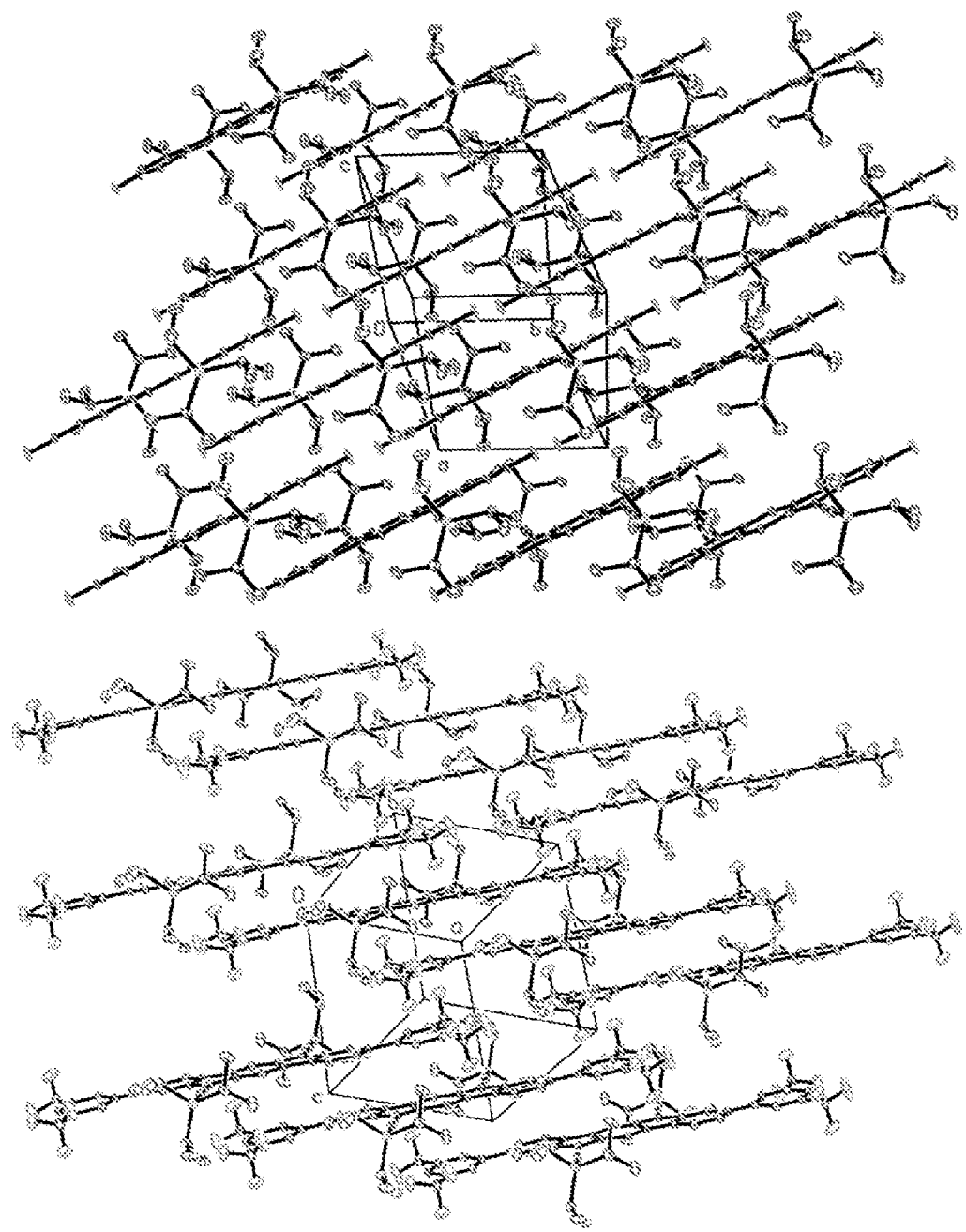
Figure 7. Crystal packing of diethynylIFs 17b (top) and 17h (bot-tom); ellipsoids drawn at the 30% probability level.

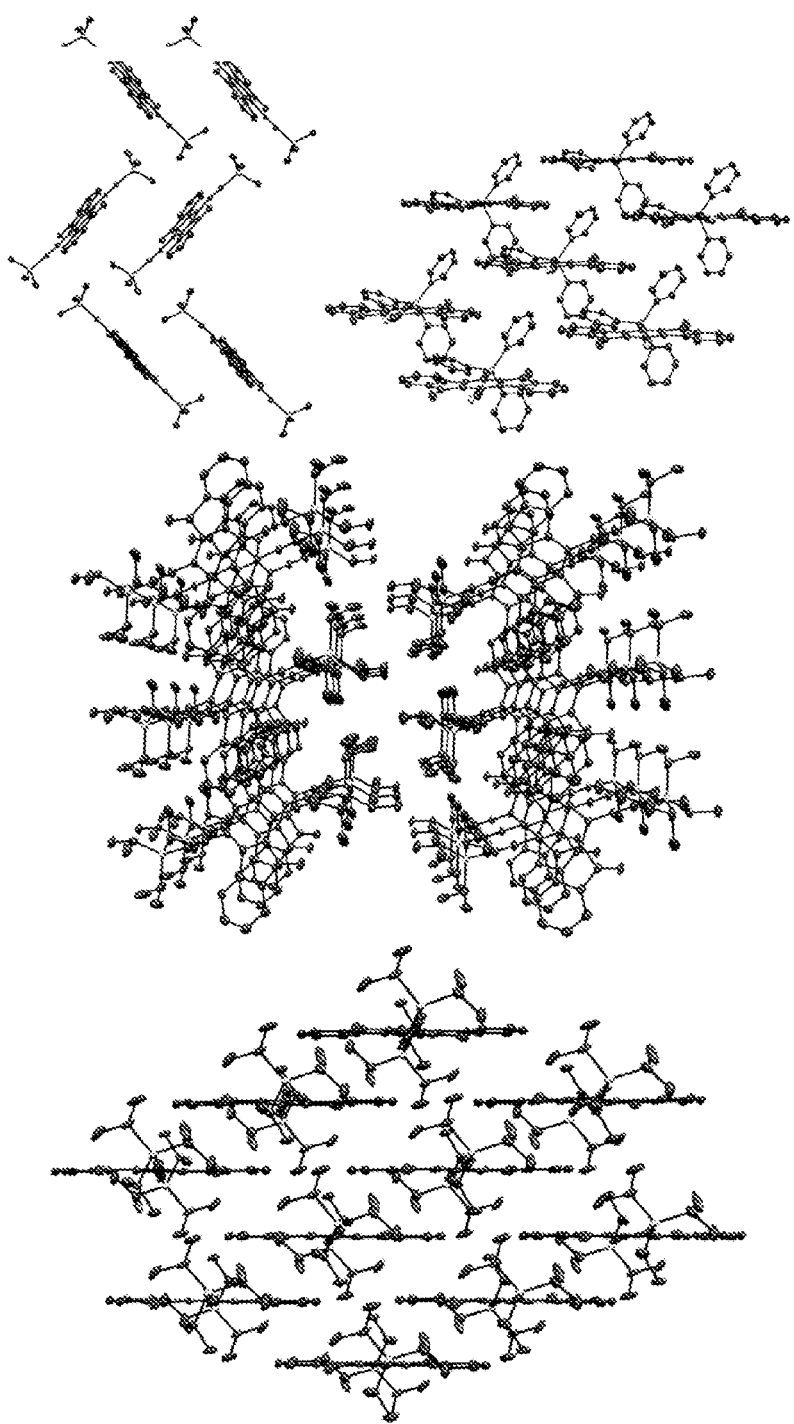
Figure 8. Crystal packing of IF-diones illustrating herringbone (20, top left), 1-D columns without π-π interactions (25, top right), and coplanar slip stacking (23, center). A side view of 23 (bottom) shows the favorable brick and mortar packing. Thermal ellipsoids drawn at the 30% probability level.

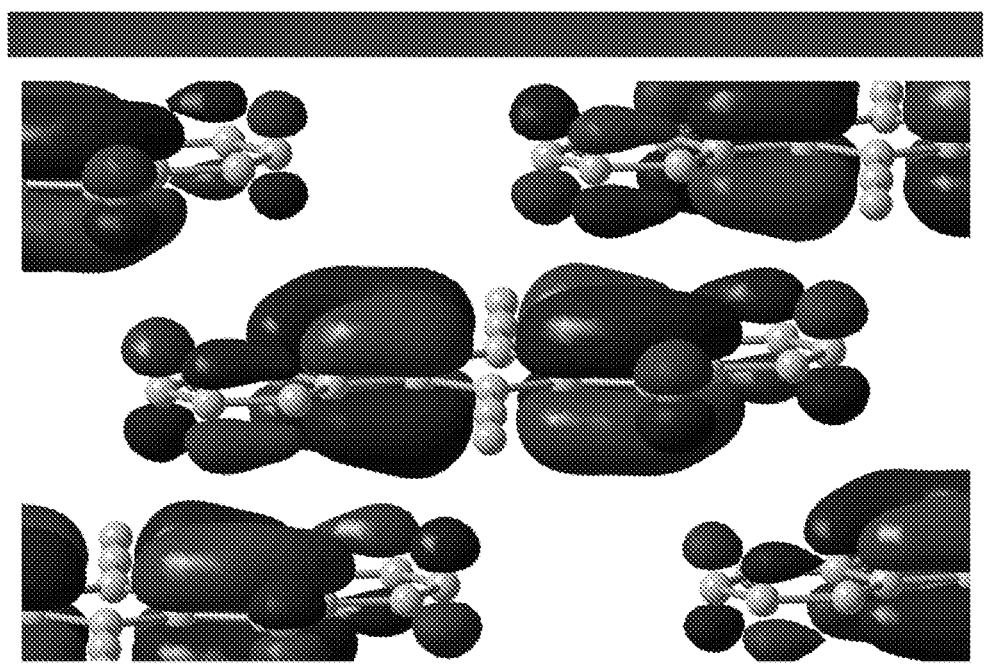
Figure 9. AM1 calculated (LUMO) interactions derived from the crystal packing in the x-ray structure of 23.

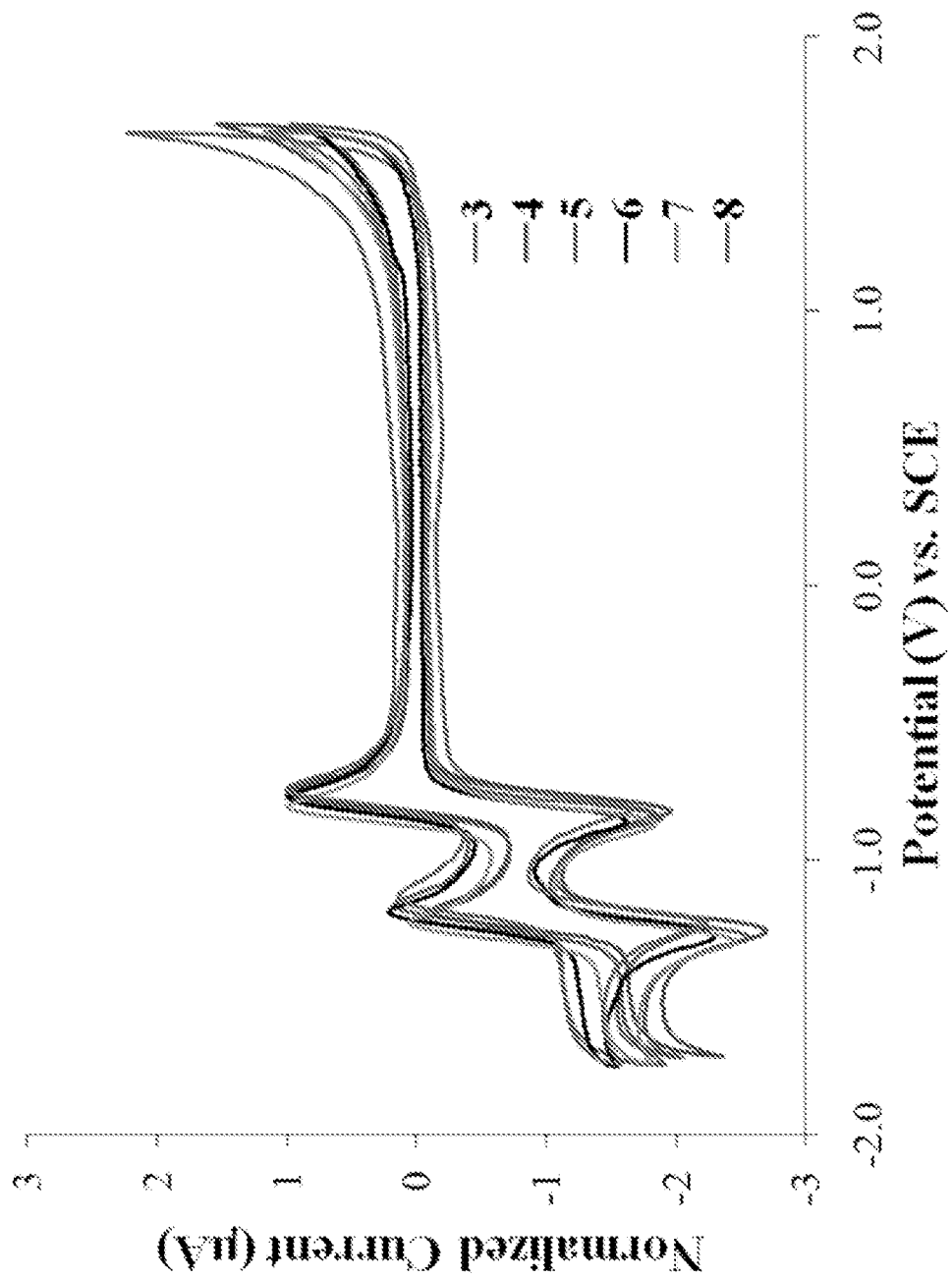
Figure 10. Cyclic voltammetry of IF-diones 20-25. Peaks are normalized to the Eox1 peak.

FIG. 11

Table 3. Experimental Optical and Electrochemical Data

| | electrochemical | | | | optical | | | |
|---|---|---|---|---|---|---|---|---|
| | $E_{red}^1$ (V)[a] | $E_{red}^2$ (V)[b] | $E_{LUMO}$ (eV)[c] | $E_{HOMO}$ (eV)[c] | $\lambda_{abs}$ (nm) | gap (eV)[d] | $\lambda_{em}$ (nm) | $\Phi_{fluorescence}$[e] |
| 20 | −0.80 | −1.21 | −3.89 | −6.38 | 310, 330, 498 | 2.49 | 571 | 0.08 |
| 21 | −0.79 | −1.23 | −3.90 | −6.39 | 311, 332, 498 | 2.49 | 569 | 0.08 |
| 22 | −0.81 | −1.25 | −3.87 | −6.36 | 312, 331, 498 | 2.49 | 571 | 0.09 |
| 23 | −0.82 | −1.24 | −3.87 | −6.35 | 313, 333, 500 | 2.48 | 568 | 0.10 |
| 24 | −0.84 | −1.26 | −3.85 | −6.34 | 314, 333, 498 | 2.49 | 567 | 0.10 |
| 25 | −0.78 | −1.18 | −3.90 | −6.40 | 312, 333, 496 | 2.50 | 570 | 0.09 |

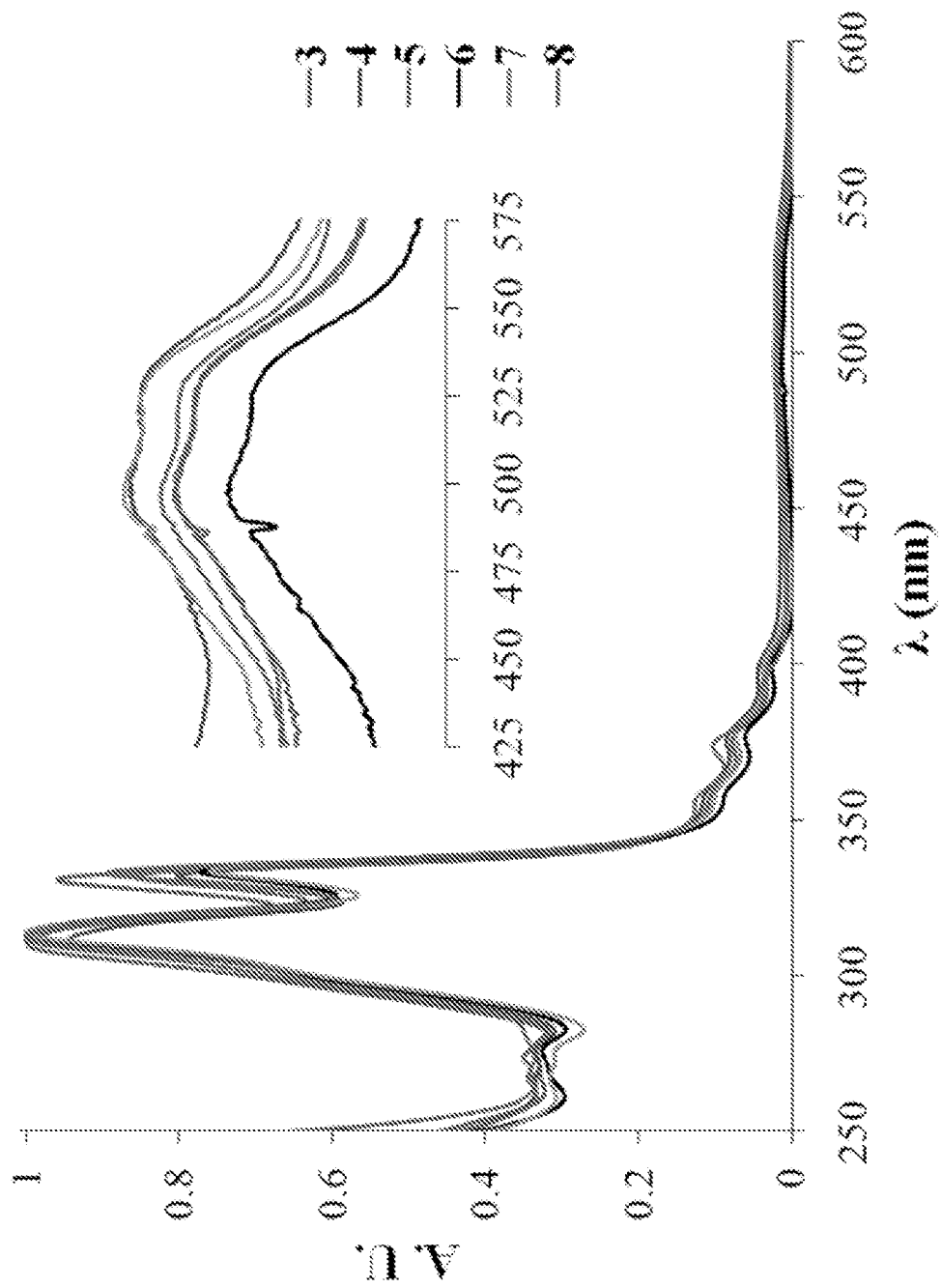
Figure 12. UV-vis data for IF-diones 20-25.

ALKYNYL-SUBSTITUTED INDENOFLUORENES USEFUL IN ELECTRONIC AND ELECTRO-OPTICAL DEVICES

CROSS REFERENCE TO RELATED APPLICATIONS

This is the U.S. National Stage of International Application No. PCT/US2011/040451, filed Jun. 15, 2011, which was published in English under PCT Article 21(2), which in turn claims the benefit of U.S. Provisional Patent Application No. 61/355,107, filed Jun. 15, 2010, and U.S. Provisional Patent Application No. 61/469,670, filed Mar. 30, 2011. Both of these applications are incorporated herein by reference in their entireties.

ACKNOWLEDGMENT OF GOVERNMENT SUPPORT

This invention was made with government support under grant NSF CHE-0718242 awarded by the National Science Foundation and NSF CHE-1013032 awarded by the National Science Foundation. The government has certain rights in the invention.

BACKGROUND

Acenes are an exciting class of compounds that have been intensely studied during the past decade. Their alluring optoelectronic properties suggest great potential as the conducting organic material in a variety of device applications such as organic light-emitting diodes (OLEDs), field-effect transistors (OFETs), and solar cells. Pentacene (compound 1) and its derivatives (e.g., compound 2) have received the vast amount of attention as this molecule has been hailed as the benchmark for thin film devices. Unfortunately, pentacene readily oxidizes to its respective quinone in aerobic conditions and reacts with itself to afford a butterfly dimer. The driving force for both reactions is the formation of two aromatic naphthalene units which ultimately disrupts overall conjugation and thus leads to poor device performance. While ethynylogation as in compound 2 or substitution with thioethers will in general slow degradation, these processes are not completely suppressed.

In addition, in the solid state pentacene packs in an edge-to-face or 'Herring Bone' conformation, which eliminates the possibility of intermolecular π-orbital interactions. Such interactions are crucial for efficient electron transfer, an important characteristic for improving device functionality and performance.

Hence, there is high demand for pentacenelike organic molecules that do not suffer from the disadvantages of pentacene, and offer greater stability to air and light.

SUMMARY

Disclosed herein are indenofluorenes, particularly alkynylated indenofluorenes.

One embodiment is a compound having a structure of:

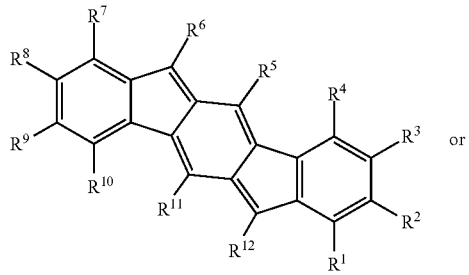

(Formula 1)

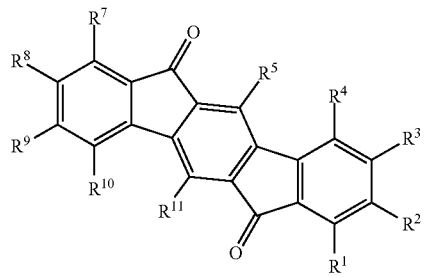

(Formula 2)

wherein $R^1$-$R^{12}$ are each individually H, amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl, provided that at least two of $R^1$-$R^{12}$ are alkynyl or substituted alkynyl.

Another embodiment is an indenofluorene that includes at least two alkynyl-containing substituents.

Also disclosed herein are electronic or electrooptical devices that include the indenofluorenes.

Also disclosed herein are processes for synthesizing the indenofluorenes including a method for making an alkynyl-substituted indeno[1,2-b]fluorene, comprising:

reacting a dione-substituted indenofluorene with an alkyne to produce a hydroxy-functional intermediate; and
reducing the hydroxy-functional intermediate to produce an alkynyl-substituted indeno[1,2-b]fluorene.

The foregoing will become more apparent from the following detailed description, which proceeds with reference to the accompanying figures.

BRIEF DESCRIPTION OF THE DRAWINGS

FIG. 4 is a table showing computational, electrochemical, and optical data for indenofluorenes disclosed herein. [a]Calculations performed at the B3LYP/6-311+G** level of theory; energies in eV. For computational efficiency, the TIPS groups of 17a-i were replaced by H atoms. [b]CV recorded using 1-5 mM of analyte in 0.1 M Bu$_4$NOTf/CH$_2$Cl$_2$ using a scan rate of 50 mV/s. The working electrode was a glassy carbon electrode with a Pt coil counter electrode and Ag wire pseudo reference. Values reported as the half-wave potential (vs. SCE) using the Fc+/Fc couple (0.46 V) as an internal standard. HOMO and LUMO energy levels were approximated using SCE=−4.2 eV vs. vacuum. Reduction potentials in V; energies in eV. [c]Spectra obtained in $CHCl_3$; wavelength in nm. [d] The optical HOMO-LUMO gap was determined as the intersection of the x-axis and a tangent line that passes through the inflection point of the lowest energy absorption; energies in eV. [e]Experimental data for 8b; computational data for 12. [f]The second reduction wave was irreversible; the potential of the peak anodic current is reported. [g]Me group in place of Bu to simplify calculations. [h] Unable to obtain. [i]Converted from Mikroyannidis, Adv. Funct. Mater. 2011, 21, 746-755.

FIG. 5 depicts the electronic absorption spectra for several indenofluorene compounds disclosed herein.

FIG. 6 depicts cyclic voltammetry of several indenofluorene compounds disclosed herein.

FIG. 7 shows crystal packing of two indenofluorene compounds disclosed herein.

FIG. 8 shows crystal packing of several indenofluorene compounds disclosed herein.

FIG. 9 is depicts AM1 calculated (LUMO) interactions derived from the crystal in the x-ray structure of an indenofluorene compound disclosed herein.

FIG. 10 depicts cyclic voltammetry of several indenofluorene compounds disclosed herein.

FIG. 11 is a table showing electrochemical and optical data for indenofluorenes disclosed herein. a CV recorded using 1-5 mM of analyte in 0.1 M etrabutylammonium trifluoromethanesulfonate/CH2Cl2 using a scan rate of 50 mV/s. The working electrode was a glassy carbon electrode with a platinum coil counter electrode and silver wire pseudo reference. Values reported as the half-wave potential (vs. SCE) using the Fc/Fc+ couple (0.46 V) as an internal standard. b Determined by ELUMO=−(4.44+Ered 1). c Calculated by subtracting the optical bandgap from the LUMO. d Determined using the maximum absorption of the lowest energy transition from the UV-vis spectrum. e Determined via the integrating sphere method.

FIG. 12 depicts UV-vis data for several indenofluorene compounds disclosed herein.

DETAILED DESCRIPTION

Terminology

Figure 1:
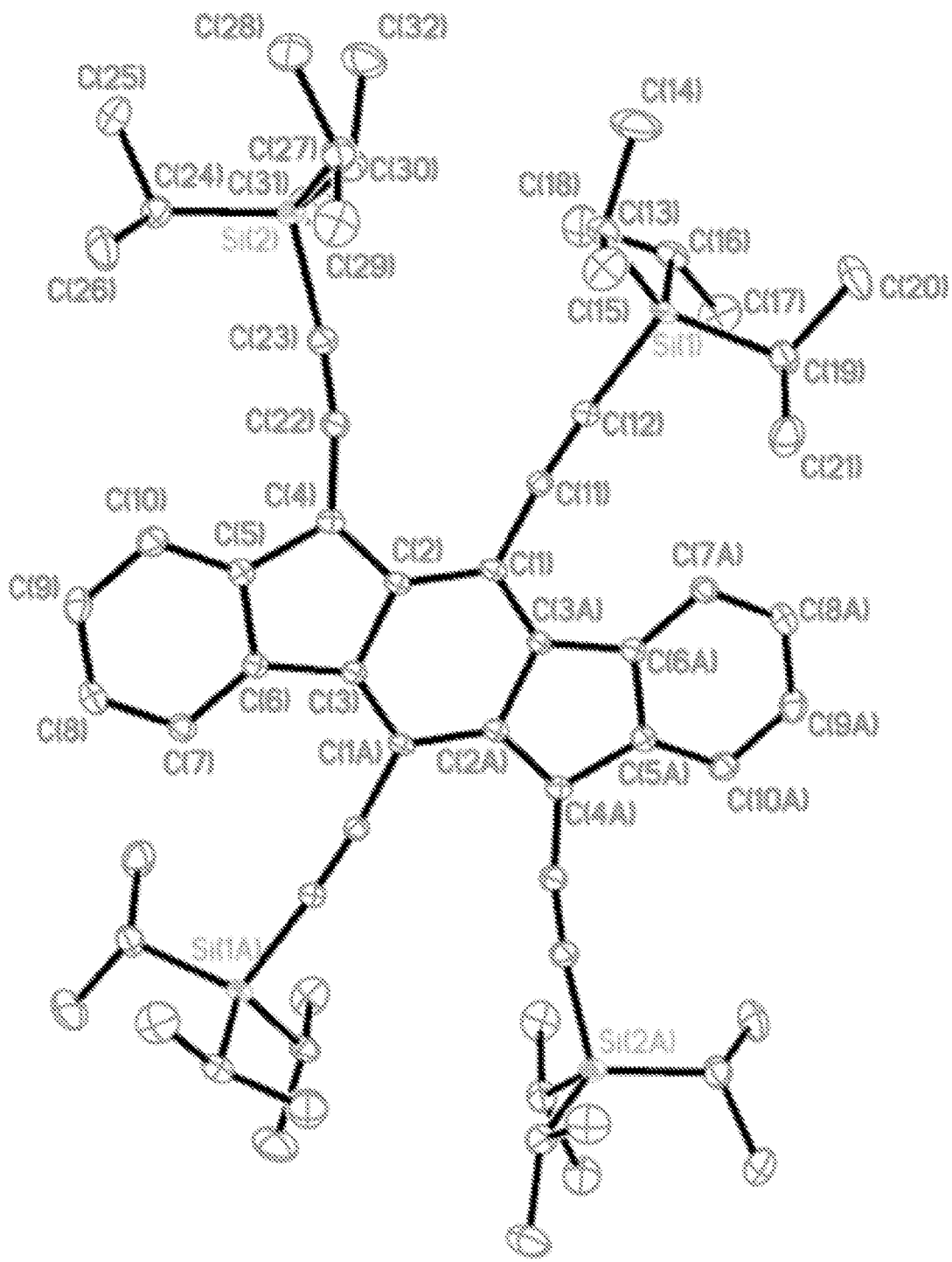
FIG. 1 shows the molecular structure of an example of an indenofluorene disclosed herein.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Also, as used herein, the term "comprises" means "includes."

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, or carboxyl.

The term "alkylaryl" refers to an aryl group having an alkyl group, as defined above, attached to the aryl group, as defined herein (—Ar—R), wherein Ar is an arylene group and R is an alkyl group.

The term "alkynyl" refers to a hydrocarbon group of 2 to 24 carbon atoms and a structural formula containing at least one carbon-carbon triple bond.

The term "alkoxy" refers to a straight, branched or cyclic hydrocarbon configuration and combinations thereof, including from 1 to 20 carbon atoms, preferably from 1 to 10 carbon atoms, more preferably from 1 to 4 carbon atoms, that include an oxygen atom at the point of attachment. An example of an "alkoxy group" is represented by the formula —OR, where R can be an alkyl group, optionally substituted with, e.g., an alkenyl, alkynyl, aryl, aralkyl, cycloalkyl, halogenated alkyl, or heterocycloalkyl group as described herein. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described herein.

The term "aralkyl" refers to an alkyl group that has at least one hydrogen atom replaced by an aryl group. An example of an aralkyl group is a benzyl group.

The term "aryl" refers to any carbon-based aromatic group including, but not limited to, benzene, naphthalene, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous. "Heterocycloalkyl" and "heterocyclic" are used interchangeably herein.

The terms "halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

The term "thioether" refers to a —S—R group, wherein R may be, for example, alkyl (including substituted alkyl), or aryl (including substituted aryl).

The term "thiol" refers to —SH. A "substituted thiol" refers to a —S—R group wherein R is not an aliphatic or aromatic group. For instance, a substituted thiol may be a halogenated thiol such as, for example, —$SF_5$.

The structural symbol  designates an ethynyl group (i.e., —C≡C—).

Overview

The indeno[1,2-b]fluorene skeleton (compound 3 below), a 6-5-6-5-6 fused ring system also known as dibenzo[a,g]-s- indacene, is an attractive alternative structural motif. A fully conjugated indenofluorene, such as those disclosed herein, should possess some remarkable characteristics: (i) compounds like 3 have two fewer carbons than pentacene and thus two fewer π-electrons, making 3 formally antiaromatic (20 π-electrons); (ii) such molecules host a p-xylylene core, an extremely reactive moiety that typically cannot be isolated due to its tendency to oligomerize/polymerize; and (iii) most importantly, indenofluorenes do not possess any internal s-cis diene linkages, which should make them resistant to the deleterious cycloaddition pathways that typically degrade pentacenes.

Although a number of molecules incorporate the indenofluorene core, nearly all bear substituents on positions 6 and 12 that either result in exocyclic conjugation (ketones 4, olefins 5) or disrupt conjugation altogether (disubstitution, spirofusion). Examples of fully-conjugated species are extremely rare, as only four compounds have been reported to date. In 1994 Swager et al. prepared and characterized tetraiodides 6 but these rapidly oxidize to the corresponding diones upon exposure to air. Very little is known about indenofluorene 7 prepared by Scherf as the synthesis was not disclosed and the only spectroscopic feature mentioned is a UV-Vis λmax absorption of 535 nm. Recently Kubo and co-workers prepared naphtho-fused indenofluorenes; however, these molecules exhibited singlet biradical behavior, meaning that the dominating resonance structure has its central benzene ring as fully aromatic and therefore could not be considered fully delocalized.

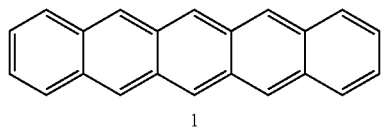

1

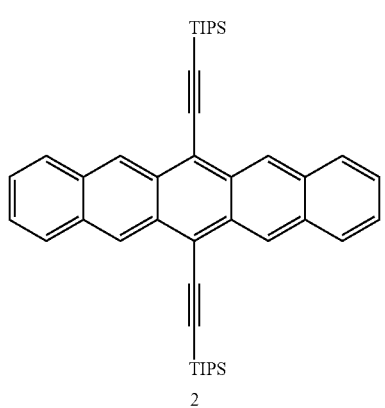

2

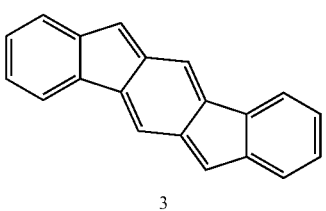

3

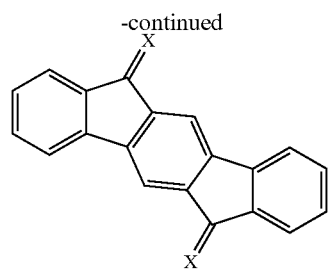

4, X = O
5, X = C(CN)$_2$

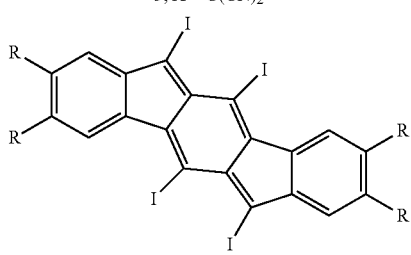

6, R = H, Dec, Dodec

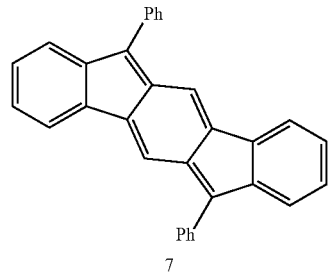

7

The indenofluorene compounds disclosed herein exhibit similar UV-Vis absorption profiles and slightly larger HOMO/LUMO energy gaps compared to pentacene (compound 1) while maintaining potentially superior solution stabilities. In addition, the indenofluorene compounds disclosed herein may provide improved resistance to photodegradation (particularly compared to compound 2). In certain embodiments, the disclosed indenofluorene compounds of Formula 1 also are non-fluorescent molecules. In certain embodiments, the disclosed indenofluorene compounds of Formula 2 are emissive. In certain embodiment, the disclosed indenofluorene compounds have a HOMO level of less than −5.5 eV, more particularly less than −5.7 eV, and most particularly less than −6.2 eV. In certain embodiments, the disclosed indenofluorene compounds have a LUMO level of less than −4 eV.

Compounds

In one embodiment, the compounds have a structure represented by:

(Formula 1)

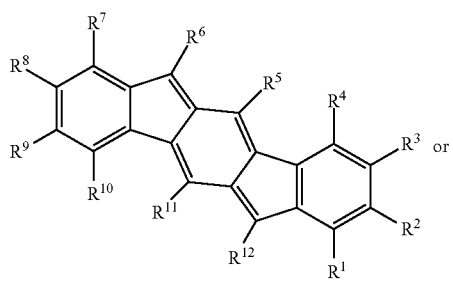

or

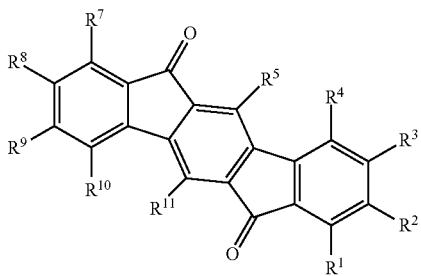

(Formula 2)

wherein $R^1$-$R^{12}$ are each individually H, amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl, provided that at least two of $R^1$-$R^{12}$ are alkynyl or substituted alkynyl.

In certain embodiments of Formula 1, $R^1$-$R^4$ and $R^7$-$R^{10}$ are each individually H, amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl; and $R^5$, $R^6$, $R^{11}$ and $R^{12}$ are each individually H, alkynyl, substituted alkynyl, amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, substituted cycloalkyl, provided that at least two of $R^5$, $R^6$, $R^{11}$ and $R^{12}$ are alkynyl or substituted alkynyl.

In certain embodiments of Formula 2, $R^1$-$R^4$ and $R^7$-$R^{10}$ are each individually H, amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, substituted cycloalkyl; and $R^5$ and $R^{11}$ are each individually alkynyl or substituted alkynyl.

In certain embodiments of Formula 1 or 2, the compound has two alkynyl or substituted alkynyl groups. In preferred embodiments of Formula 1, the two alkynyl or substituted alkynyl groups are located at the $R^6$ and $R^{12}$ positions. In other embodiments of Formula 1 or 2, two alkynyl or substituted alkynyl groups are located at the $R^5$ and $R^{11}$ positions. In further embodiments, the compound has four alkynyl or substituted alkynyl groups. In preferred embodiments of Formula 1, the four alkynyl or substituted alkynyl groups are located at the $R^5$, $R^6$, $R^{11}$ and $R^{12}$ positions. In certain embodiments of Formula 1 or 2, the alkynyl or substituted alkynyl groups may be located at $R^2$, $R^3$, $R^8$, and $R^9$ positions. In preferred embodiments of Formula 1 or 2 all of the alkynyl or substituted alkynyl groups of the compound are identical. For example, the compound may have two ethynyl groups or two TIPSethynyl groups. In another embodiment of Formula 1, the alkynyls or substituted alkynyls at the $R^5$ and $R^{11}$ positions are identical, and the alkynyls or substituted alkynyls at the $R^6$ and $R^{12}$ positions are identical. For example, the compound may have an ethynyl group at each of the $R^5$ and $R^{11}$ positions and a TIPSethynyl group at each of $R^6$ and $R^{12}$ positions.

In certain embodiments, the alkynyl or substituted alkynyl may be a $C_2$-$C_{10}$, more particularly $C_2$-$C_5$, alkynyl or substituted alkynyl (e.g., —C≡CR). In preferred embodiments, the alkynyl or substituted alkynyl is ethynyl or substituted ethynyl. The substituted alkynyl may be substituted with a silyl-containing group, a hydrocarbyl derivative of a silyl group such as an alkyl silyl (particularly tri-$C_1$-$C_6$ alkylsilyls), an aryl silyl (particularly tri-arylsilyls), or an alkoxy silyl (particularly tri-$C_1$-$C_6$ alkoxysilyls), a tin-containing group, or a germanium-containing group. Illustrative substituents for the substituted alkynyl include —Si(isopropyl)$_3$ (i.e., "TIPS"), —Si(n-propyl)$_3$, —Si(n-butyl)$_3$, —Si(isobutyl)$_3$, —Si(tert-butyl)$_3$, —Si(sec-butyl)$_3$, —Si(ethyl)$_3$, —Si(methyl)$_3$, —Si(tert-butyl)(methyl)$_2$, —Si(c-pentyl)$_3$, —Si(c-hexyl)$_3$, —Si(phenyl)$_3$, —Si(Si(methyl)$_3$)$_3$.

In certain embodiments of Formula 1 at least two of $R^5$, $R^6$, $R^{11}$ and $R^{12}$ are alkynyl or substituted alkynyl as described above (preferably $R^6$ and $R^{12}$); $R^1$, $R^3$, $R^4$, $R^7$, $R^9$, and $R^{10}$ are each H; and $R^2$ and $R^8$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl. Preferably, $R^2$ and $R^8$ are identical moieties (e.g., $R^2$ and $R^8$ are each F, or are each methyl).

In certain embodiments of Formula 1 at least two of $R^5$, $R^6$, $R^{11}$ and $R^{12}$ are alkynyl or substituted alkynyl as described above (preferably $R^6$ and $R^{12}$); $R^1$, $R^2$, $R^4$, $R^7$, $R^8$, and $R^{10}$ are each H; and $R^3$ and $R^9$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl. Preferably, $R^3$ and $R^9$ are identical moieties.

In certain embodiments of Formula 1 at least two of $R^5$, $R^6$, $R^{11}$ and $R^{12}$ are alkynyl or substituted alkynyl as described above (preferably $R^6$ and $R^{12}$); $R^3$, $R^2$, $R^4$, $R^8$, $R^9$, and $R^{16}$ are each H; and $R^1$ and $R^7$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl. Preferably, $R^1$ and $R^7$ are identical moieties.

In certain embodiments of Formula 1 at least two of $R^5$, $R^6$, $R^{11}$ and $R^{12}$ are alkynyl or substituted alkynyl as described above (preferably $R^6$ and $R^{12}$); $R^1$-$R^4$ and $R^7$-$R^{10}$ are each individually H; and two of $R^5$, $R^6$, $R^{11}$ and $R^{12}$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl. Preferably, $R^5$, $R^6$, $R^{11}$ and/or $R^{12}$ are identical moieties.

In certain embodiments of Formula 1 at least two of $R^5$, $R^6$, $R^{11}$ and $R^{12}$ are alkynyl or substituted alkynyl as described above (preferably $R^6$ and $R^{12}$); and $R^1$-$R^4$ and $R^7$-$R^{10}$ are each individually H.

In certain embodiments of Formula 2, $R^1$, $R^3$, $R^4$, $R^7$, $R^9$, and $R^{10}$ are each H; and $R^2$ and $R^8$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl. Preferably, $R^2$ and $R^8$ are identical moieties (e.g., $R^2$ and $R^8$ are each F, or are each methyl).

In certain embodiments of Formula 2, $R^1$, $R^2$, $R^4$, $R^7$, $R^8$, and $R^{10}$ are each H; and $R^3$ and $R^9$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl. Preferably, $R^3$ and $R^9$ are identical moieties.

In certain embodiments of Formula 2, $R^3$, $R^2$, $R^4$, $R^8$, $R^9$, and $R^{10}$ are each H; and $R^1$ and $R^7$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl. Preferably, $R^1$ and $R^7$ are identical moieties.

In certain embodiments of Formula 2, $R^1$-$R^4$ and $R^7$-$R^{10}$ are each individually H; and two of $R^5$, $R^6$, $R^{11}$ and $R^{12}$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl. Preferably, $R^5$, $R^6$, $R^{11}$ and/or $R^{12}$ are identical moieties.

In certain embodiments of Formula 2, $R^1$-$R^4$ and $R^7$-$R^{10}$ are each individually H.

Illustrative groups for $R^1$-$R^{12}$ for Formula 1 or 2 (in addition to the alkynyl-containing moieties described above) are halogen (e.g., F, Cl, Br), $C_1$-$C_{10}$ alkyl (e.g., methyl, ethyl, propyl, decyl), aryl (e.g., phenyl), substituted alkyl (e.g., halogenated $C_1$-$C_{10}$ alkyl such as —$CF_3$), substituted aryl (e.g., halogenated phenyl such as —$C_6F_5$, 4-$CF_3C_6H_4$, or 3,5-$(CF_3)_2C_6H_3$), $C_1$-$C_{10}$ alkoxy (e.g., methoxy), a $C_1$-$C_{10}$ alkyl-substituted thiol (e.g., —$SF_5$), thioether (e.g., —SMe or —SBu), a sulfur-containing heteroaryl (e.g., a thienyl), —$NO_2$, —CN, or an alkyl-substituted sulfur-containing heteroaryl (e.g., 2-(5-$BuC_4H_2S$).

In certain embodiments of Formula 1 or 2 the groups for $R^1$-$R^{12}$ may be electron-withdrawing or electron-donating. The electron-withdrawing groups may decrease the HOMO and LUMO levels of the compounds. The electron-donating groups may decrease the HOMO/LUMO gap energies of the compounds. In preferred embodiments, electron-donating groups may be located at the $R^2$, $R^3$, $R^8$, and/or $R^9$ positions. In particular, electron-donating groups are located at the $R^2$ and $R^8$ positions. Illustrative electron-withdrawing groups include F, Cl, Br, $CF_3$, $C_6F_5$, 3,5-$(CF_3)_2C_6H_3$, CN, $NO_2$, and $SF_5$. Illustrative electron-donating groups include —OR, —SR, amino, alkylaryl groups (including diaryl groups), polycyclic aryl groups (e.g., pentacenyl, and fluorenyl). Several specific electron-donating groups are shown below:

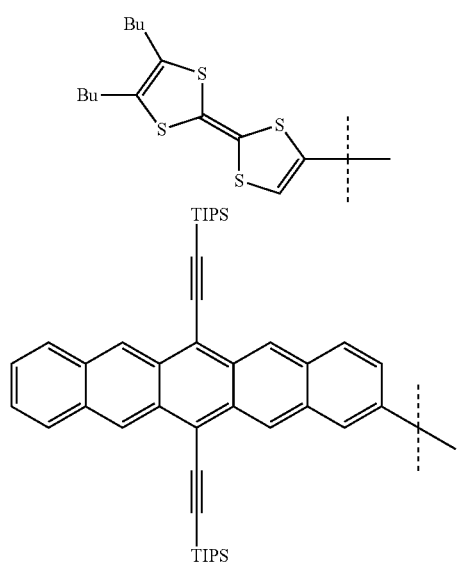

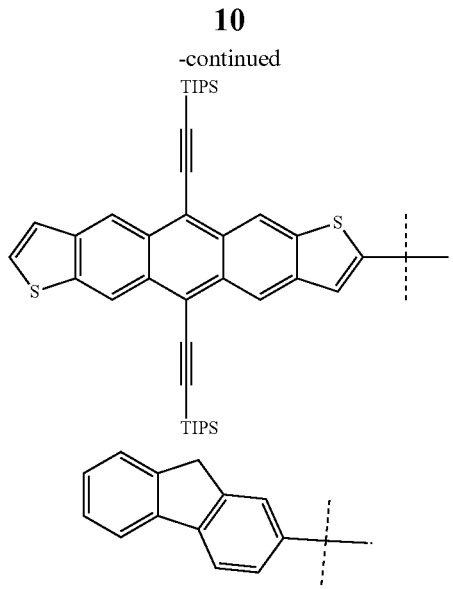

The substitution of one or more non-hydrogen substituents on the indenofluorene ring system may be used to fine tune the spectral properties of the resulting indenofluorene compound of formula 2. Generally, the excitation and emission wavelengths can be shifted according to the electron-withdrawing/electron-donating strength and number of such substituents.

Specific, non-limiting, examples of compounds are shown below:

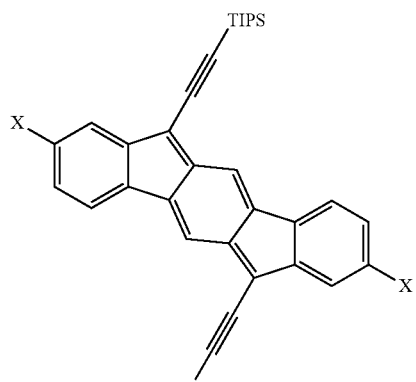

wherein X=F, Cl, Br, Me, or Ph

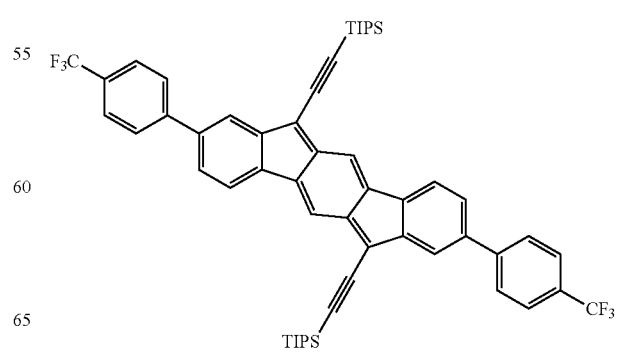

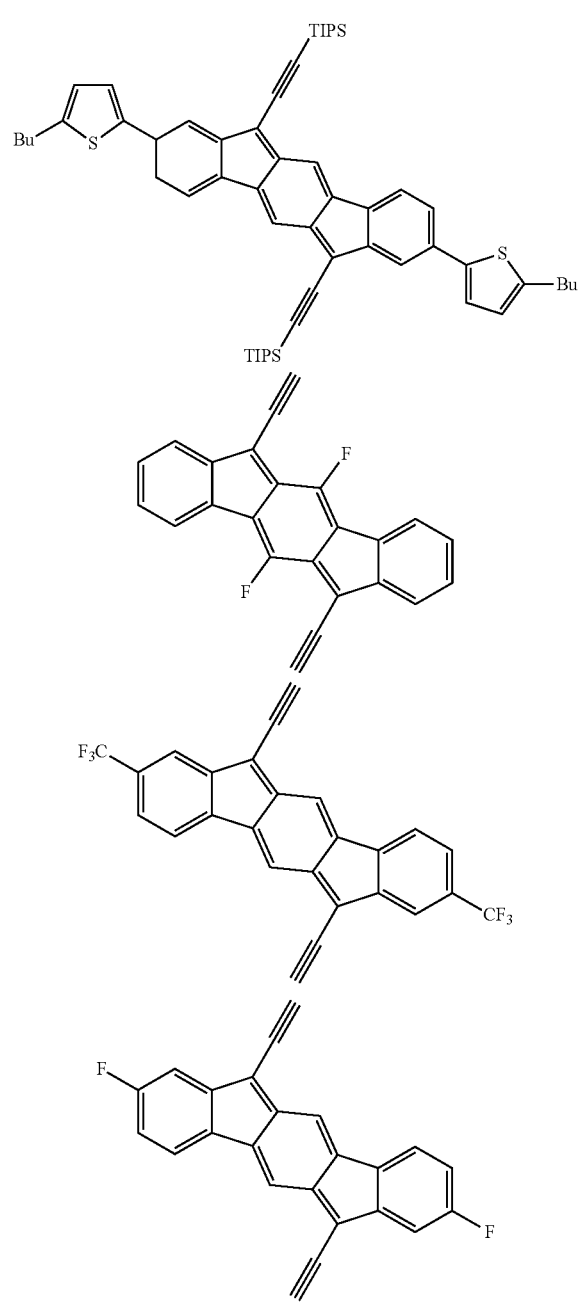

Synthesis

Initial attempts to access the tetraethynylated derivatives via Sonogashira cross-coupling directly to 6a proved to be problematic, affording complex mixtures of products. Instead, the syntheses of indenofluorenes 8a-b introduced the alkynes in a stepwise manner. Starting with known diiododiones 9a-b, cross-coupling with TIPSA afforded diynes 10a-b (see Scheme 1). Addition of the lithiated acetylide of TIPSA and subsequent reduction of the intermediate diols 11 using SnCl$_2$ in acid provided 8a-b in low to modest overall yield. While red in the solid state, solutions of 8a-b exhibit a brilliant blue color.

Scheme 1. Syntheses of 8a-b.

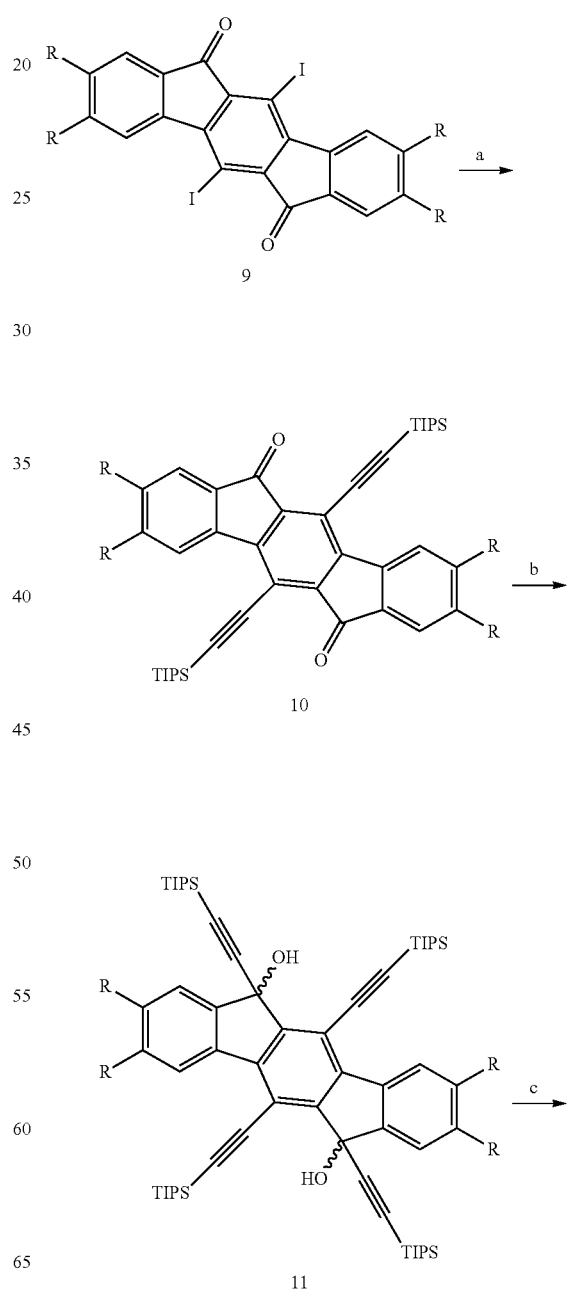

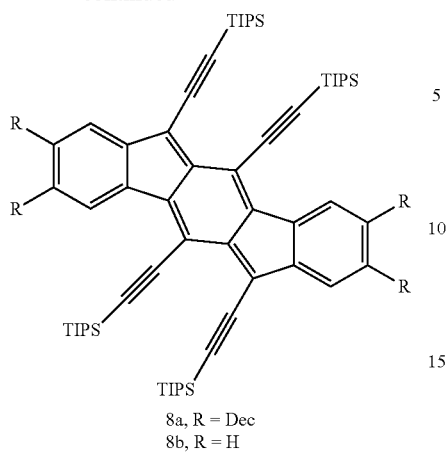

8a, R = Dec
8b, R = H a) TIPSA, Pd(PPh₃)₂Cl₂, CuI, THF, iPr2NH, 60° C., 44% for 10a, 32% for 10b;
b) TIPSC≡CLi, THF, -78° C.; c) SnCl₂•H2O, THF, 83% (2 steps) for 8a, 27% (2 steps) for 8b.

An alternative synthetic route to the indenofluorene compounds is shown below:

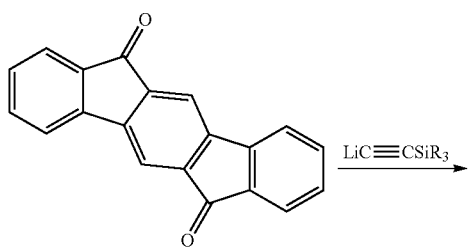

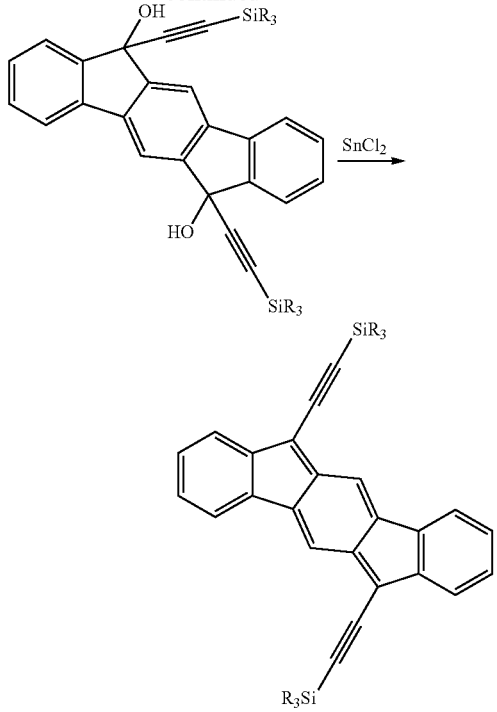

where the SiR₃ moieties offer site for the synthetic introduction of desired functional groups as described above. A variety of dione-substituted indenofluorenes are commercially available or can be easily synthesized as described in Merlet et al, Org. Lett. 2002, 4, 2157,2160. Thus, the use of dione-substituted indenofluorenes (such as 6,12-diones) as the starting material offers a wide variety of possible alkynylated indenofluorenes. It is evident that the positions of the oxo groups on the indenofluorene core structure of the starting material correspond to the same positions as the alkynyl groups on the end product. The hydroxy-functional intermediate is reduced to produce an alkynyl-substituted indeno[1,2-b]fluorene. Although the above scheme is shown with SiR₃, a silylated group is not required meaning that the alkynyl group can be substituted with any R group or it may be terminated with a H atom.

A further synthetic scheme for making multi-functional alkynylated indenofluorenes is shown below:

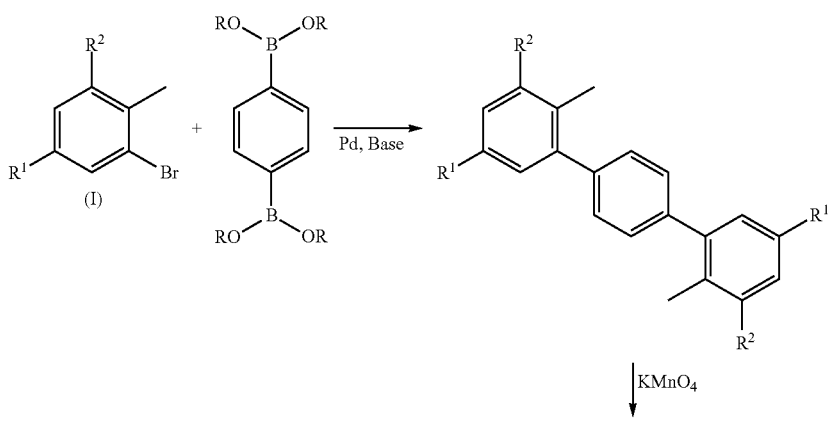

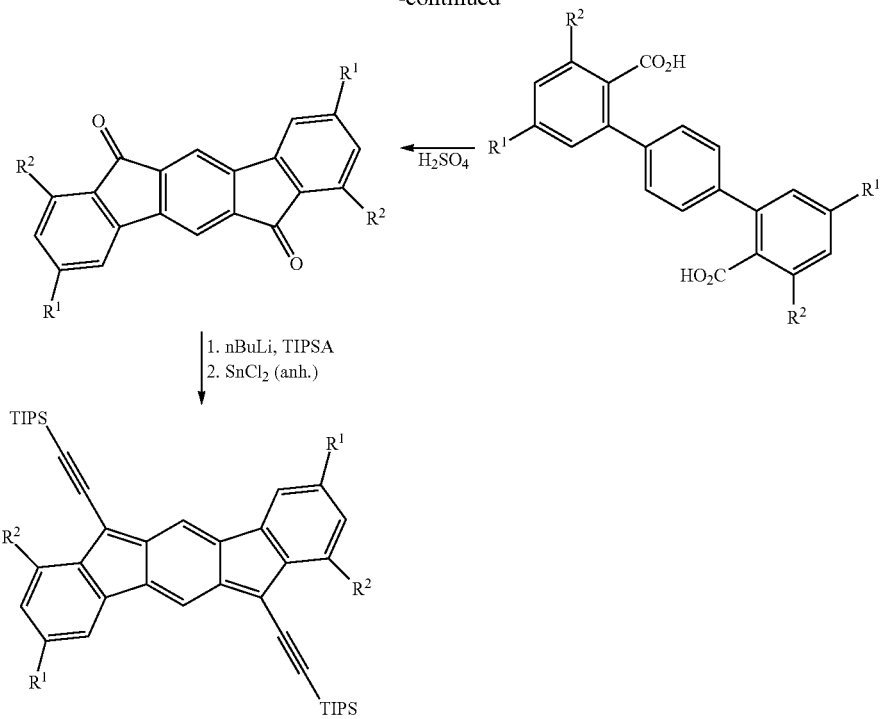

R = H, alkyl
R¹ = Br, Cl, F, CF₃, etc.
R² = H, Br, Cl, F, CF₃, etc.

Compound Applications

The indenofluorene compounds disclosed herein may be used in electronic or electrooptical devices such as, for example, an organic light-emitting diode (OLED), an organic field effect transistor (OFET), or an organic photovoltaic cell (OPV). The indenofluorenes disclosed herein may be used as organic semiconductors in form of thin organic layers or films, for example, less than 30 microns thick. For instance, the semiconducting layer is at most 1 micron thick, although it may be thicker if required. For various electronic device applications, the thickness may also be less than about 1 micron thick. For use in an OFET, the layer thickness may typically be 500 nm or less, in an OLEDs be 100 nm or less. The exact thickness of the layer will depend, for example, upon the requirements of the electronic device in which the layer is used.

For example, the active semiconductor channel between the drain and source in an OFET may comprise a layer that includes the indenofluorene. As another example, a hole injection or transport layer, and or an electron blocking layer in an OLED device may comprise a layer that includes the indenofluorene.

An OFET may comprise: a source electrode, a drain electrode, a gate electrode, a semiconducting layer, one or more gate insulator layers, optionally a substrate, wherein the semiconductor layer comprises one or more indenofluorenes as described herein.

In certain embodiments the photovoltaic cell includes an anode, a cathode, and a semiconductor layer or film that includes at least one of the indenofluorene compounds disclosed herein.

EXAMPLES

Example 1

Trialkylsilyl-dialkynyl-substituted indeno[1,2-b]fluorenes

Two exemplary indenofluorene compounds are shown above the stable, fully conjugated indenofluorenes 8a and 8b (see Scheme 1, above). An X-ray crystal structure of 8b unambiguously confirms its planar, fully conjugated state and provides a rare glimpse into the p-xylylene core. Also disclosed are the absorption and emission profiles of 8a and 8b as well as their stability to photooxidative conditions in comparison to 2.

Compounds 8a and 8b were synthesized as described above according to scheme 1. Single crystals of 8b suitable for x-ray diffraction were obtained by slow evaporation of a solution in hexanes. The molecular structure of 8b (FIG. 1) reveals that fused ring system is essentially planar (deviation<0.0x Å). The bulky TIPS-capped acetylenes are bent away from one another by 4-11° yet also remain in the plane of the 20-carbon core. Our initial hypothesis regarding bond lengths consisted of two possibilities: (1) the overall antiaromaticity of the molecule would dominate, resulting in alternating long and short bonds throughout the entire ring system; or (2) the benzene rings would remain fully delocalized and the p-xylylene unit would possess long and short bond lengths as typical for non-aromatic single and double bonds, that is a dibenzo[12]annulene. Examination of the C—C bond lengths (Table 1) indicates that indeed there are alternating long (1.438(3) and 1.457(3) Å for C1-C2 and C2-C3, respectively) and short (1.374(3) and 1.390(3) Å for C1-C3A and C2-C4, respectively) bonds in the central p-xylylene core but the peripheral benzene bond lengths are relatively homogenized (1.392-1.412 Å). To shed additional light, NICS(1) calculations for the desilylated analog of 8a revealed that the NICS values for the peripheral, five-membered, and central rings to be −7.12, −1.84, and 0.02, respectively. The B3LYP/6-311+G**—optimized geometry of 8b (Table 1) provided bond lengths of 1.444, 1.457, and 1.379 Å for C1-C2, C2-C3, and C1-C3A, respectively, and 1.393 to 1.418 Å for bond lengths of the peripheral arene rings, values which nearly coincide with the crystallographic data. Lower level semi-empirical calculations performed by Kataoka et al. also corroborate these findings. Such good agreement between the data suggests that neither initial hypothesis was correct. Instead, 8b should be considered a fully conjugated 20 π-electron hydrocarbon with fused s-trans 1,3-diene linkages across both the top and bottom portions of the carbon skeleton. Interestingly, this bonding situation closely resembles that of Thiele's and Chichibabin's hydrocarbons, the only previously reported X-ray data analyses of molecules containing the p-xylylene core.

TABLE 1

Bond lengths of 8b and related molecules.

| Bond | X-Ray | DFT Calcs[a] | SCF MO Calcs | Thiele's Hydrocarbon |
|---|---|---|---|---|
| C1-C3A | 1.374(3) | 1.379 | 1.365 | 1.346 |
| C2-C3 | 1.438(3) | 1.444 | 1.457 | 1.449 |
| C2-C3 | 1.457(3) | 1.457 | 1.462 | 1.449 |
| C2-C4 | 1.390(3) | 1.396 | 1.371 | 1.381 |
| C3-C6 | 1.470(3) | 1.466 | 1.470 | [b] |
| C4-C5 | 1.470(3) | 1.463 | 1.456 | [b] |
| C5-C6 | 1.412(3) | 1.417 | 1.411 | [b] |
| Benzene (avg) | 1.389(3) | 1.398 | 1.402 | [b] |

[a]Performed using B3LYP/6-311 + G**
[b]Not present in crystal.

Figure 2:
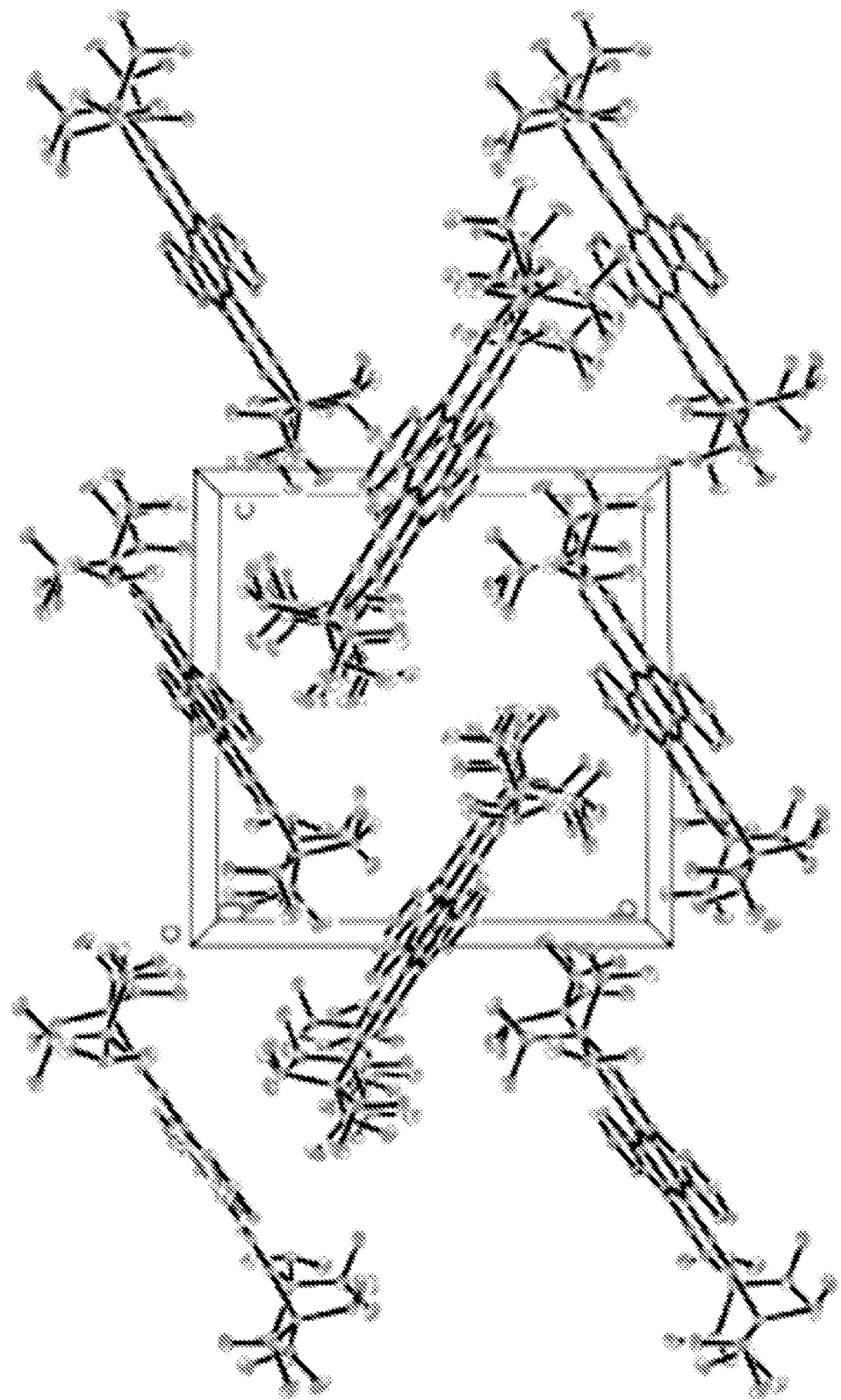
FIG. 2 shows the crystal packing of an example of an indenofluorene disclosed herein.

The crystal packing of 8b (FIG. 2) loosely resembles the herringbone pattern often found in unsubstituted acenes such as pentacene. The presence of the four interdigitated TIPS groups per indenofluorene expands this motif, yet the packing is sufficiently tight that no solvent molecules are co-crystallized with 8b. The major contacts in the unit cell are between the TIPS groups and the central IF ring with an average distance of 3.93 Å.

Figure 3:
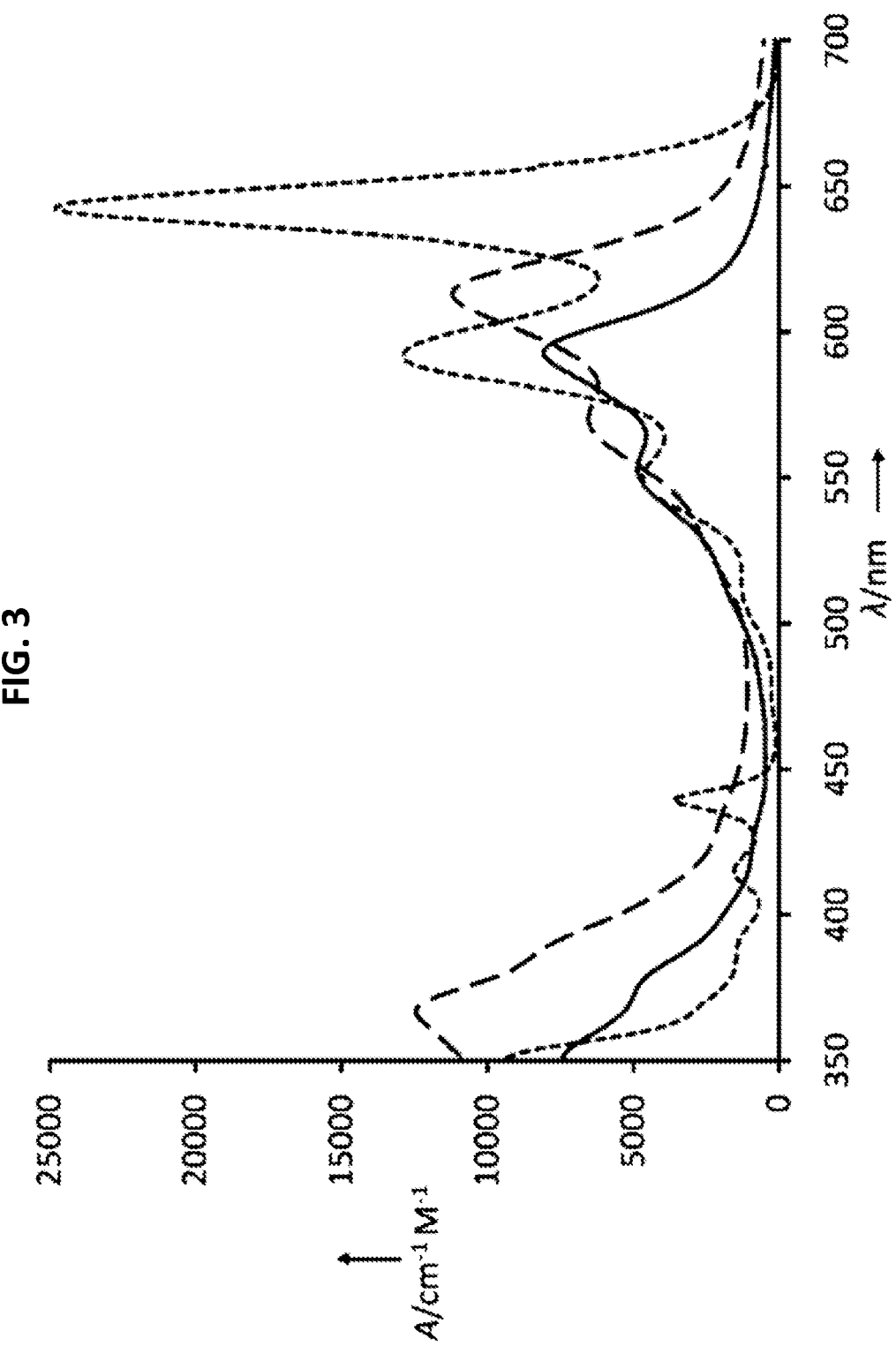
FIG. 3 is a graph showing the electronic absorption spectra of compound 2) (-------) and two examples of indenofluorenes disclosed herein (compound 8a (-----) and compound 8b (------------).

The absorption and emission spectra of 8a and 8b are shown along with 2 in FIG. 3. Similar to pentacene 2, indenofluorenes 8a and 8b both exhibit three low energy absorptions (λmax: 614 and 594 nm, respectively) but are blue-shifted (30 and 50 nm, respectively). These optical data correspond to estimated HOMO-LUMO gaps of 1.98 and 1.91 eV for 8b and 8a, respectively, compared to 1.85 eV for 2, which agree quite well with the B3LYP/6-311+G**— calculated gap of 1.97 eV for the desilylated analog of 8b. Unlike 2, both 8b and 8a are non-emissive, which is usually the case with [4n] π-electron systems.

The relative stabilities of 8a and 8b were also examined. Initial testing by UV/Vis spectroscopy was performed under similar conditions as reported by Miller et al., *J. Am. Chem. Soc.* 2008, 10, 16274-16286, but no degradation was observed in the time frame used for their pentacene studies (<12 h). Instead, samples of 8a and 8b were allowed to stand in loosely capped volumetric flasks under air in the light, and periodic 1H NMR measurements were made. While it was found that samples of 8a and 8b were stable on the order of a few weeks, the molecules eventually did degrade over the course of 2-3 months.

Example 2

6,12-diethynylindeno[1,2-b]fluorene Derivatives

As a guide for experimental studies, DFT calculations (B3LYP/6-311+G**) were performed on a variety of substituted IFs. The initial task was to determine the effect ethynylogation of indeno[1,2-b]fluorene (compound 3) has on the HOMO (−5.53 eV) and LUMO energy levels (−3.03 eV) and energy gap (2.50 eV) of the IF core (see compounds below, Table 2 of FIG. 4).

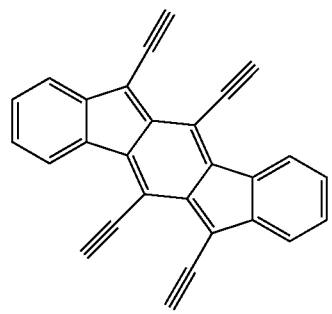

12

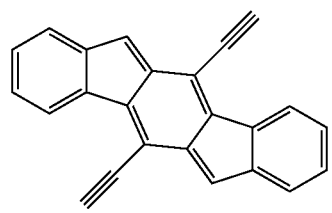

13

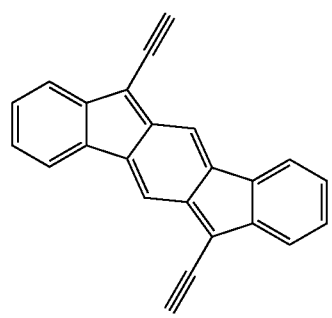

14

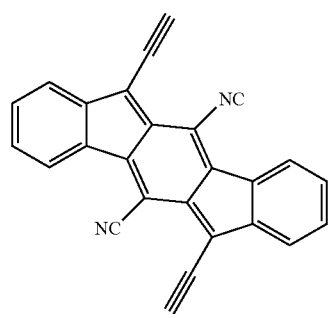

15

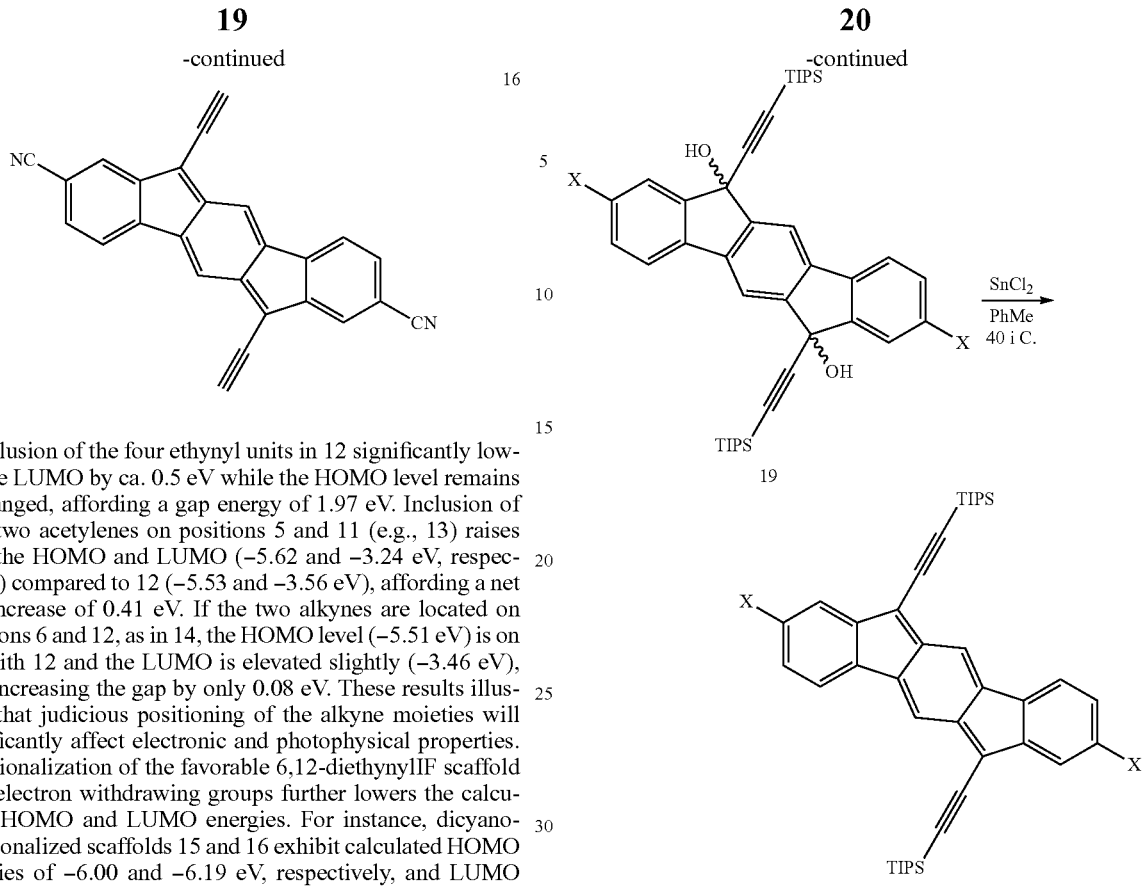

a, X = H (71%)
b, X = F (31%)
c, X = Cl (35%)
d, X = Br (47%)
e, X = Me (60%)
f, X = Ph (44%)
g, X = 4-CF$_3$C$_6$H$_4$ (43%)
h, X = 3,5-(CF$_3$)$_2$C$_6$H$_3$ (62%)
i, X = 2-(5-BuC$_4$H$_2$S) (81%)

Inclusion of the four ethynyl units in 12 significantly lowers the LUMO by ca. 0.5 eV while the HOMO level remains unchanged, affording a gap energy of 1.97 eV. Inclusion of only two acetylenes on positions 5 and 11 (e.g., 13) raises both the HOMO and LUMO (−5.62 and −3.24 eV, respectively) compared to 12 (−5.53 and −3.56 eV), affording a net gap increase of 0.41 eV. If the two alkynes are located on positions 6 and 12, as in 14, the HOMO level (−5.51 eV) is on par with 12 and the LUMO is elevated slightly (−3.46 eV), thus increasing the gap by only 0.08 eV. These results illustrate that judicious positioning of the alkyne moieties will significantly affect electronic and photophysical properties. Functionalization of the favorable 6,12-diethynylIF scaffold with electron withdrawing groups further lowers the calculated HOMO and LUMO energies. For instance, dicyano-functionalized scaffolds 15 and 16 exhibit calculated HOMO energies of −6.00 and −6.19 eV, respectively, and LUMO energies of −4.07 and −4.14 eV, respectively. Such molecules may be suitable n-type organic semiconductors, as these energy levels and gaps closely resemble those of ubiquitous electron acceptor PCBM (−6.2 and −3.95 eV). Encouraged by these initial computational studies, a number of 6,12-diethynylindeno[1,2-b]fluorenes were targeted for synthesis and study. Disclosed herein the preparation of IFs 17a-i along with their respective optical, electrochemical and computational data. We also report the X-ray structures of 17b and 17h, highlighting the effects that substitution on the IF core has on crystal packing.

Since the transannular cyclization route used in Scheme 1 above to synthesize the IF core was low yielding, intolerant of facile substitution, and difficult to scale up, a more efficient pathway was sought resulting in the development of Scheme 2 below.

Scheme 2

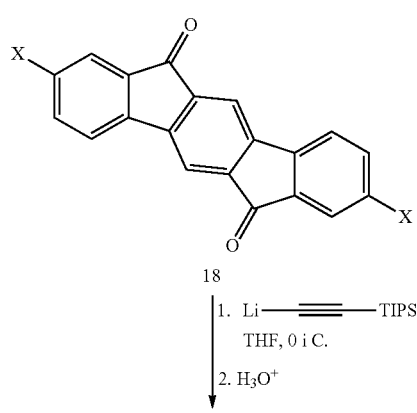

Fortunately, dione 18a is readily synthesized on multi-gram scale via the three-step Suzuki/Friedel-Crafts route devised by Merlet et al., Org. Lett. 2002, 4, 2157-2159. Addition of lithiated (triisopropylsilyl)acetylene afforded crude diol 19a; subsequent reduction using SnCl$_2$ in toluene at 40° C. provided a deep magenta solution, from which IF 17a was isolated in very good yield. This methodology could be extended to a number of 2,8-disubstituted IFs starting from the respective diones, either known (18b-d) or easily synthesized (18e-i).

The absorption spectra of 8b and 17a,b,i are shown in FIG. 5. Similar to 8b, IF 17a exhibits three low-energy absorptions ($\lambda_{max}$ 567 nm), but these are blue-shifted ca. 25-30 nm compared to 8b. This can be attributed to removal of the two acetylenes at the 5 and 11 positions in 17a. Interestingly, variation of the substituents bound to the IF core at the 2 and 8 positions has only modest effect on the absorption profiles: fluoro IF 17b has the lowest $\lambda_{max}$ value of 561 nm, whereas the max of thienyl IF 17i is at 577 nm. The optical data correspond to a relatively narrow 2.08-2.15 eV range for the HOMO-LUMO energy gaps of 17a-i. As observed with 8b, 17a-i are non-emissive, as is usually the case with [4n] π-electron systems.

FIG. 6 depicts the experimental cyclic voltammetry (CV) data for 8b and 17a,b,h. In solution, the IFdiyne scaffold shows quasi-reversible behavior, accepting up to two electrons. The first reduction half-wave potential at ca. −0.5 to −0.7 V (vs. SCE) for 17a-h is 0.2-0.3 V less negative than the diynyl IF-diones. These data suggest that IFs have comparable or greater electron affinities to that of PCBM. Substitution of electron withdrawing groups on the IF core shifts the reduction half-wave potentials to less negative values. This is chiefly observed with parent 17a, fluoro 17b, and 3,5-$(CF_3)_2$ $C_6H_3$ 17h, which possess first reduction half-wave potentials of −0.69, −0.60, and −0.52 V, respectively. This trend is pronounced even further where 17a, 17b, and 17h exhibit second reduction half-wave potentials of −1.20, −1.07, and −1.00 V, respectively. Unlike the IF-diones, 17a-h also exhibit irreversible oxidation around 1.2-1.3 V. The above-mentioned trend also holds true for peak potentials for oxidation of the IF scaffold; substitution of increasing electron withdrawing groups shifts the potential to more positive values as demonstrated by 17a, 17b, and 17h, which exhibit peak potentials of 1.20, 1.33, and 1.35 V, respectively. This behavior is justified by examining the products of reduction or oxidation: a two-electron reduction of the IF core results in a 22 π-electron species where every ring is aromatic, i.e., three benzenes and two Cp anions. Hence, an increase in electron withdrawing capability would better stabilize the dianion. Conversely, the formation of oxidative products, especially the 18 π-electron dication, would be destabilized by electron-withdrawing groups. The sole exception to the above mentioned behavior is 17i, which exhibits an irreversible reduction and polymerizes under oxidative conditions.

Interestingly, while the electrochemically determined energy gaps are somewhat lower (1.85-1.94 eV) than the optical and computational values, all three data sets exhibit a<0.1 eV range of values, whether substituted with electron-rich or electron-poor groups. Examination of the calculated HOMO-LUMO plots for 17a reveals that the 2- and 8-positions possess little orbital density, and hence exhibit virtually no overlap. Therefore, perturbing the electronic nature of the IF scaffold from these positions can be performed only through weak inductive effects. Single crystals of 17b and 17h suitable for X-ray diffraction were obtained from $CH_2Cl_2/CH_3CN$ and $CHCl_3$, respectively (FIG. 7). Similar to 8b, the molecular structures of 17b and 17h show that the fused ring system is essentially planar (within 0.017 and 0.042 Å, respectively); however, unlike 8b, the TIPS-capped acetylenes in both species are nearly linear (179°) and planar (0.5° deviation) with the 20-carbon-atom core, which is due to the fact that these lack the steric congestion that 8b possesses. Furthermore, the C—C bonds in the central six-membered ring are slightly compressed (0.02 Å) compared to 8b. In the crystal lattice IFs 17b and 17h are organized as 1-D π-stacks with close C•••C contacts of 3.43 and 3.40 Å, respectively. The 1-D π-stacks in 17b form a layer with a shift between two nearest π-stacks. Such an arrangement avoids strong π-interactions between the π-stacks in the layers, but some of C•••C contacts between 1-D π-stacks are in the range 3.14-3.50 Å, indicating that weak interactions between 1-D π-stacks in 17b are possible. On the other hand, the 1-D π-stacks in the crystal of 17h are isolated without specific interactions between them. Additionally, the peripheral 3,5-$(CF_3)_2C_6H_3$ groups for 17 h are nearly coplanar with the IF core, exhibiting a slight 5.5° twist, which is much less than the 35-45° torsion angle typically seen in most biphenyls. This unexpected co-planarity is likely due to the enhanced overlap the phenyl rings provide as they lay directly above and below the central arene of the neighboring molecules as well as the interdigitation of two electron deficient —$CF_3$ groups with electron rich alkynes (3.50 Å intermolecular distance). The above examples demonstrate a facile approach to a family of fully conjugated indeno[1,2-b]fluorenes. The optical and electrochemical data support the computational findings of low-lying HOMO and LUMO energy levels for 17a-i. These values are similar to PCBM and other mainstream n-type semiconductors, suggesting that IFs could be compliments to the usually p-type acenes. Through X-ray crystallography, 17b and 17h were shown to pack in dimeric π-stacks in the solid-state, which further improves their credibility for materials applications.

Example 3

Ethynylated Indenofluorenediones

An important indicator of potential device performance when using organic molecules is the solid state ordering of the material, which is currently difficult to predict using theoretical modeling. It is well known that the mobilities of holes (for p-type) or electrons (for n-type) in solid state organic materials are increased when both the intermolecular overlap of the π orbitals is maximized and those orbitals are in phase.

Compounds 20-25 were synthesized in low to moderate yields by Sonogashira cross-coupling of the appropriate (trialkylsilyl)acetylene with 26 (Scheme 3). One possible explanation for the low isolated yields is the lability of iodine atoms of 26. Solutions of 26 at elevated temperatures turn pale violet, characteristic of iodine formation; however, the Sonogashira reaction proceeds sluggishly at temperatures less than 50° C. Orange single crystals of 20 and 23 suitable for x-ray diffraction were grown by slowly cooling of hot hexanes solutions of the IF-diones, whereas 25 was recrystallized by slow evaporation from a binary combination of THF and hexanes.

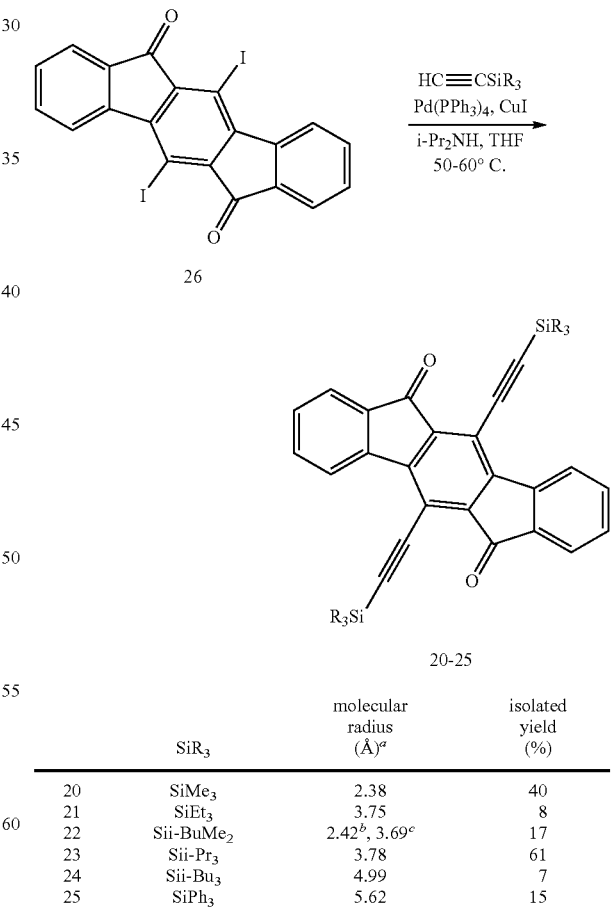

Scheme 3. Synthesis of Alkynylated Indenofluorenediones

| SiR₃ | molecular radius (Å)[a] | isolated yield (%) |
|---|---|---|
| 20 | SiMe₃ | 2.38 | 40 |
| 21 | SiEt₃ | 3.75 | 8 |
| 22 | Sii-BuMe₂ | 2.42[b], 3.69[c] | 17 |
| 23 | Sii-Pr₃ | 3.78 | 61 |
| 24 | Sii-Bu₃ | 4.99 | 7 |
| 25 | SiPh₃ | 5.62 | 15 |

[a]Measured using the internuclear distance from the silicon to the farthest atom of R.
[b]Si—Me distance.
[c]Si—iPr distance.

Similar to conjugated systems such as acenes, the IF-diones exhibit three types of packing in the solid state: (i) herringbone packing (e.g. 20, FIG. 8 top left), (ii) 1-dimensional columns without π-π interactions (e.g. 25, FIG. 8, top right) and (iii) coplanar slip stacking (e.g. 23, FIG. 8 center and bottom). This last arrangement, also known as brick and mortar packing, was found only in 23 and maximizes the π-π interactions in two dimensions (FIG. 8 bottom) with an interplanar distance of 3.40 Å, in contrast to the interplanar distance of 3.77 Å in 25. The situation for 23 is reminiscent to 6,13-bis[(triisopropylsilyl)ethynyl]pentacene, which showed coplanar slip stacking as well. (Anthony et al, J. Am. Chem. Soc. 2001, 123, 9482). Anthony attributed this phenomenon to the diameter of the triisopropylsilyl (TIPS) group being close to the stack spacing needed for intermolecular π-π interactions (3.4 Å). Interestingly, previous crystal structures of IF-diones have also displayed herringbone packing with slip stacked 1-dimensional π-π interactions, 4c lamellar 1-dimensional stacks, 4d or essentially no π-π interactions. (Usta, J. Am. Chem. Soc. 2009, 131, 5586).

Another consideration is the phase as well as the amount of orbital overlap in the crystal lattice. As can be seen in FIG. 9, the semi-empirical single point calculation based on the crystal structure of 23 shows that the orbitals are indeed in phase with orbital overlap between eight carbons between each molecule in one direction and four carbons in the other. Hence the crystal packing of 23 possesses significant orbital interaction in one direction and less in the other.

The B3LYP/6-311+G(d,p) minimized structure of 20 gives the energy levels of the HOMO at −6.28 eV and LUMO at −3.24 eV. Replacing the SiMe3 groups with H atoms alters the calculated HOMO/LUMO values to −6.43 and −3.33 eV, respectively, illustrating the weak influence of the silyl substituent. These calculated numbers are in excellent agreement with the experimental cyclic voltammetry (CV) data, shown in FIG. 10 and compiled in FIG. 11, Table 3. In solution the IF-dione scaffold is capable of reversibly accepting up to two electrons, typically at low potentials due to the low lying LUMO energy levels. The first reduction half-wave potential at ca. −0.81 V (vs. SCE) for 20-25 is indeed lower than the unsubstituted parent IF-dione (−1.19 V), which can be attributed to the electron withdrawing ethynyl moiety. In comparison to other known IF-diones, the first reduction half-wave potential of 20-25 is lower than the 3,9-halogenated-IF-diones (−1.02 to −1.08 V), comparable to 6,12-didodecyl-3,9-dibromo-IF-dione (−0.77 V) and greater than 1,2,3,4,7,8,9,10-octafluoro-6,12-diiodo-IFdione (−0.45 V). No oxidation process was observed, analogous to previous IF-diones.

The UV-vis spectra of 20-25 (FIG. 12) exhibit intense absorptions at approximately 312 and 330 nm due to the π→π transitions. Very weak bands appear at ca. 500 nm and are attributed to the symmetry forbidden n→π* transition of the carbonyl groups. The fluorescence spectra of 20-25 (not shown) exhibit a single broad peak around 570 nm, with quantum yields in the range of 8-10%.

The above data demonstrates that these compounds (particularly compound 23) may be solution processable n-type semiconductors.

In view of the many possible embodiments to which the principles of the disclosed invention may be applied, it should be recognized that the illustrated embodiments are only preferred examples of the invention and should not be taken as limiting the scope of the invention.

What is claimed is:

1. A compound having a structure of:

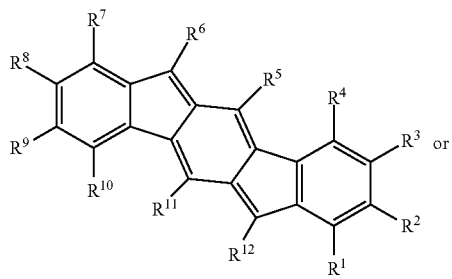

(Formula 1)

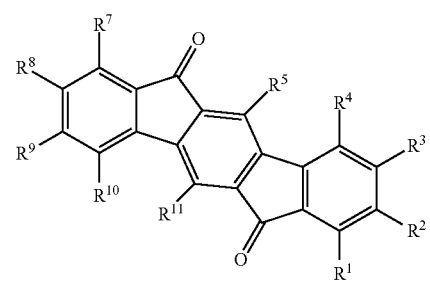

(Formula 2)

wherein $R^1$-$R^{12}$ are each individually H, amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl, provided that at least two of $R^1$-$R^{12}$ are alkynyl or substituted alkynyl, and in Formula 2 the substituted alkynyl is substituted with a silyl, an alkyl silyl, an aryl silyl, an alkoxy silyl, a tin-containing group, or a germanium-containing group.

2. The compound of claim 1, wherein the compound is of formula 1 and $R^1$-$R^4$ and $R^7$-$R^{10}$ are each individually H, amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl; and $R^5$, $R^6$, $R^{11}$ and $R^{12}$ are each individually H, alkynyl, substituted alkynyl, amino, halogen, alkyl, aryl, substituted alkyl, substituted aryl, nitro, alkoxy, substituted alkoxy, cyano, thiol, thioether, hydroxyl, heteroaryl, substituted heteroaryl, cycloalkyl, or substituted cycloalkyl, provided that at least two of $R^5$, $R^6$, $R^{11}$ and $R^{12}$ are alkynyl or substituted alkynyl.

3. The compound of claim 1, wherein the compound is of formula 2, and $R^1$-$R^4$ and $R^7$-$R^{10}$ are each individually H, amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl; and $R^5$ and $R^{11}$ are each individually alkynyl or substituted alkynyl.

4. The compound of claim 2, wherein $R^6$ and $R^{12}$ are each alkynyl or substituted alkynyl.

5. The compound of claim 2, wherein $R^5$, $R^6$, $R^{11}$ and $R^{12}$ are each alkynyl or substituted alkynyl.

6. The compound of claim 2, wherein the alkynyl is ethynyl or the substituted alkynyl is substituted ethynyl.

7. The compound of claim 1, wherein the substituted alkynyl in Formula 1 is substituted with a silyl, an alkyl silyl, an aryl silyl, an alkoxy silyl, a tin-containing group, or a germanium-containing group.

8. The compound of claim 1, wherein $R^1$, $R^3$, $R^4$, $R^7$, $R^9$, and $R^{10}$ are each H, and $R^2$ and $R^8$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl.

9. The compound of claim 8, wherein $R^2$ and $R^8$ are identical moieties.

10. The compound of claim 1, wherein $R^1$, $R^4$, $R^7$, and $R^{10}$ are each H, and $R^2$, $R^3$, $R^8$ and $R^9$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl.

11. The compound of claim 10, wherein $R^2$, $R^3$, $R^8$ and $R^9$ are identical moieties.

12. The compound of claim 1, wherein $R^1$, $R^2$, $R^4$, $R^7$, $R^8$, and $R^{10}$ are each H, and $R^3$ and $R^9$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl.

13. The compound of claim 12, wherein $R^3$ and $R^9$ are identical moieties.

14. The compound claim 1, wherein $R^3$, $R^2$, $R^4$, $R^8$, $R^9$, and $R^{10}$ are each H, and $R^1$ and $R^7$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl.

15. The compound of claim 14, wherein $R^1$ and $R^7$ are identical moieties.

16. The compound of claim 2, wherein $R^1$-$R^4$ and $R^7$-$R^{10}$ are each individually H.

17. The compound of claim 1, wherein $R^1$-$R^4$ and $R^7$-$R^{10}$ are each individually H, and two of $R^5$, $R^6$, $R^{11}$ and $R^{12}$ are each individually amino, halogen, alkyl, aryl, substituted alkyl, substituted aryl, nitro, alkoxy, substituted alkoxy, cyano, thiol, thioether, hydroxyl, heteroaryl, substituted heteroaryl, cycloalkyl, or substituted cycloalkyl.

18. The compound of claim 17, wherein $R^5$ and $R^6$ or $R^{11}$ and $R^{12}$ are identical moieties.

19. The compound of claim 1, wherein at least two of $R^1$-$R^4$ and $R^7$-$R^{10}$ are not H.

20. The compound of claim 2, wherein each alkynyl or substituted alkynyl is the identical moiety.

21. An electronic or electrooptical device that includes the compound of claim 1.

22. The device of claim 21, wherein the device is an organic light-emitting diode (OLED), an organic field-effect transistor (OFET), or an organic photovoltaic cell (OPV).

23. The device of claim 21, wherein the compound of claim 1 is an n-type organic semiconductor.

24. The device of claim 21, wherein the device is an organic photovoltaic cell (OPV).

25. The device of claim 21, wherein the device is an organic light-emitting diode (OLED), or an organic field-effect transistor (OFET).

26. The compound of claim 2, wherein the compound is

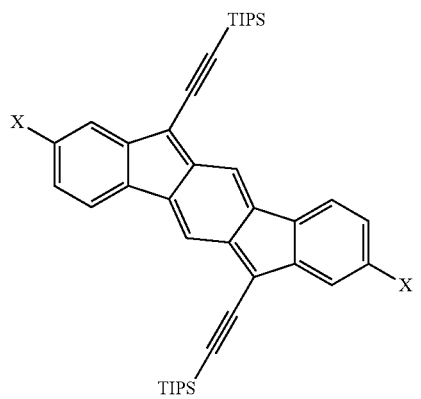

wherein X=F, Cl, Br, Me, or Ph,

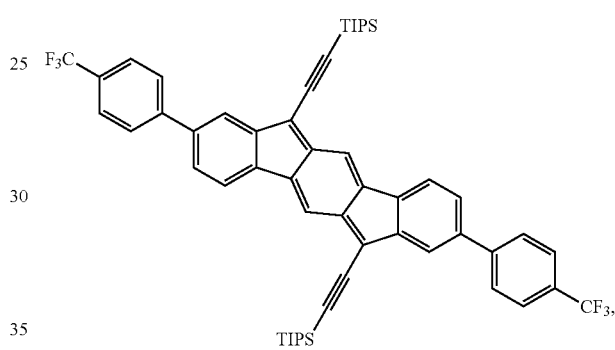

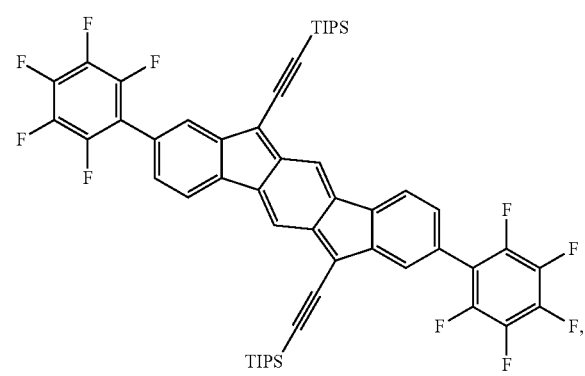

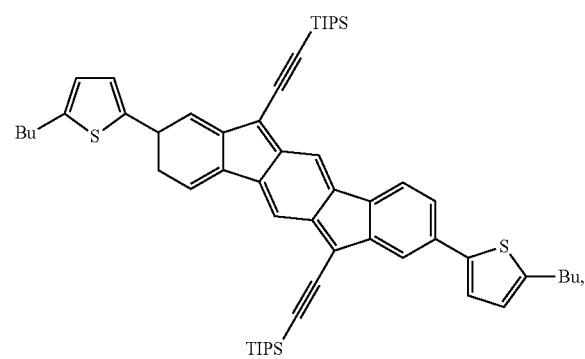

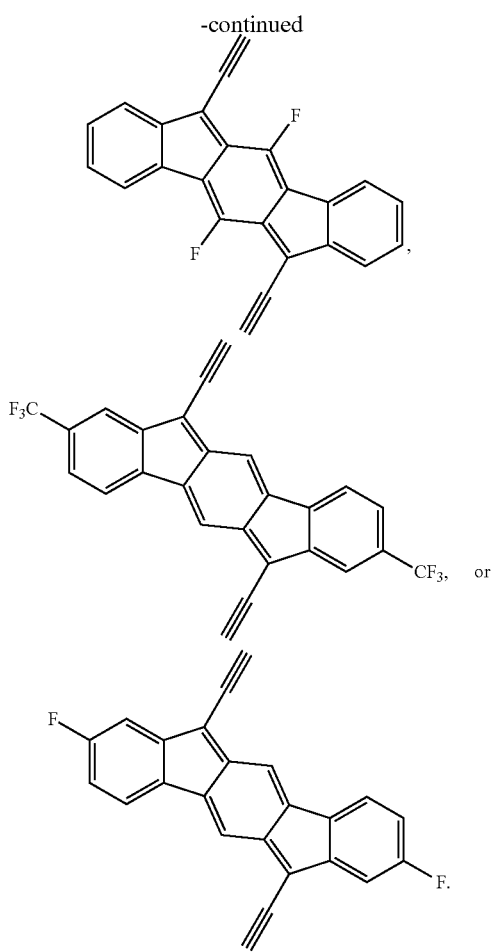

27. A compound having a structure of:

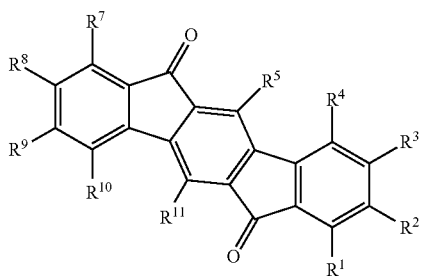

(Formula 2)

wherein $R^1$, $R^3$, $R^4$, $R^7$, $R^9$, and $R^{10}$ are each H, $R^2$ and $R^8$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl, and $R^5$ and $R^{11}$ are alkynyl or substituted alkynyl.

28. A compound having a structure of:

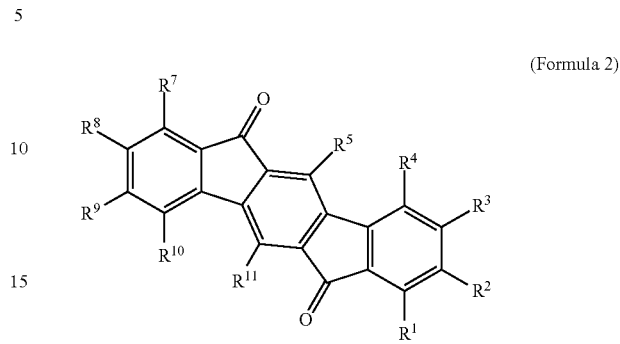

(Formula 2)

wherein $R^1$, $R^4$, $R^7$, and $R^{10}$ are each H, $R^2$, $R^3$, $R^8$ and $R^9$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl, and $R^5$ and $R^{11}$ are alkynyl or substituted alkynyl.

29. A compound having a structure of:

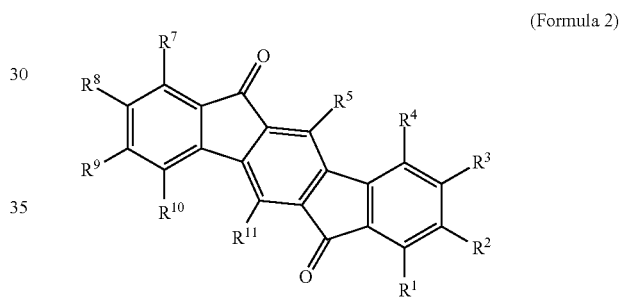

(Formula 2)

wherein $R^3$, $R^2$, $R^4$, $R^8$, $R^9$, and $R^{10}$ are each H, $R^1$ and $R^7$ are each individually amino, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl, and $R^5$ and $R^{11}$ are alkynyl or substituted alkynyl.

30. The compound of claim 1, wherein at least two of $R^1$-$R^{12}$ are alkynyl.

31. An electronic or electrooptical device that includes the compound of claim 7.

32. An electronic or electrooptical device that includes the compound of claim 27.

33. An electronic or electrooptical device that includes the compound of claim 28.

34. An electronic or electrooptical device that includes the compound of claim 29.

* * * * *